(12) United States Patent
Song et al.

(10) Patent No.: US 10,054,569 B2
(45) Date of Patent: Aug. 21, 2018

(54) METHOD AND SYSTEM FOR LIQUID CHROMATOGRAPHY FLUIDIC MONITORING

(75) Inventors: Tao Song, Milford, MA (US); John E. Brann, Shrewsbury, MA (US); Joseph J. Takarewski, Brookline, MA (US); Eric A. France, Quincy, MA (US)

(73) Assignee: Thermo Finnigan LLC, San Jose, CA (US)

( * ) Notice: Subject to any disclaimer, the term of this patent is extended or adjusted under 35 U.S.C. 154(b) by 1071 days.

(21) Appl. No.: 14/353,278

(22) PCT Filed: Apr. 25, 2012

(86) PCT No.: PCT/US2012/034895
§ 371 (c)(1),
(2), (4) Date: Apr. 21, 2014

(87) PCT Pub. No.: WO2013/062624
PCT Pub. Date: May 2, 2013

(65) Prior Publication Data
US 2014/0299542 A1 Oct. 9, 2014

Related U.S. Application Data

(63) Continuation-in-part of application No. PCT/US2011/058230, filed on Oct. 28, 2011.
(Continued)

(51) Int. Cl.
*G01N 30/32* (2006.01)
*G01N 30/88* (2006.01)
*G01M 3/28* (2006.01)

(52) U.S. Cl.
CPC .......... *G01N 30/32* (2013.01); *G01M 3/2815* (2013.01); *G01N 30/88* (2013.01);
(Continued)

(58) Field of Classification Search
CPC .. G01N 30/32; G01N 30/36; G01N 2030/326; G01N 2030/328; G01N 2030/889
See application file for complete search history.

(56) References Cited

U.S. PATENT DOCUMENTS 4,980,296 A  12/1990 Trisciani et al.
5,664,937 A   9/1997 Takahashi et al.
(Continued)

FOREIGN PATENT DOCUMENTS

CN       2872061 Y    2/2007
CN    101925812 A    6/2014
(Continued)

OTHER PUBLICATIONS

Agilent, "Agilent 1200 Series Quaternary Pump," User Manual, G1311-90011, (Nov. 2008), pp. 1-150.
(Continued)

*Primary Examiner* — Robert Clemente
(74) *Attorney, Agent, or Firm* — Thomas F. Cooney

(57) ABSTRACT

A method for monitoring a fluidic system of a liquid chromatography system is characterized by: (a) drawing a fluid into a syringe pump; (b) configuring a valve so as to fluidically couple the pump to either a fluidic pathway through the fluidic system or to a plug that prevents fluid flow; (c) causing the syringe pump to progressively compress the fluid therein or expel the fluid to the fluidic pathway, while measuring a pressure of the fluid; (d) determining a profile of the variation of the measured pressure; (e) comparing the determined profile to an expected profile that depends upon the fluid; and (f) providing a notification of a sub-optimal operating condition or malfunction if the determined profile varies from the expected profile by greater than a predetermined tolerance.

10 Claims, 23 Drawing Sheets

Related U.S. Application Data

(60) Provisional application No. 61/408,046, filed on Oct. 29, 2010.

(52) U.S. Cl.
CPC . *G01N 2030/326* (2013.01); *G01N 2030/328* (2013.01); *G01N 2030/889* (2013.01)

(56) References Cited

U.S. PATENT DOCUMENTS

| | | |
|---|---|---|
| 6,461,515 B1 | 10/2002 | Safir et al. |
| 2006/0062878 A1 | 3/2006 | Ruppe et al. |
| 2007/0089493 A1 | 4/2007 | Allington et al. |
| 2011/0005304 A1 | 1/2011 | Vorm |
| 2011/0162447 A1 | 7/2011 | Kirk et al. |
| 2011/0174737 A1 | 7/2011 | Liu et al. |
| 2011/0202188 A1 | 8/2011 | Pensak, Jr. et al. |
| 2011/0259451 A1 | 10/2011 | Weissgerber |

FOREIGN PATENT DOCUMENTS

| | | |
|---|---|---|
| EP | 0153712 A2 | 9/1985 |
| EP | 2244091 A1 | 10/2010 |
| JP | 2005-128030 A | 8/2005 |
| JP | 2005257690 | 9/2005 |
| WO | WO 2005/050190 A2 | 6/2005 |
| WO | WO 2005/091924 A2 | 10/2005 |
| WO | 2009/059292 A1 | 5/2009 |

OTHER PUBLICATIONS

Agilent, "Agilent 1260 Infinity Binary Pump VL," User Manual, G1312-90008, (Feb. 2012), pp. 1-222.

U.S. Appl. No. 13/881,886; excerpt from Final-Rejection dated Feb. 11, 2015.

U.S. Appl. No. 13/881,886; excerpt from Non-Final-Rejection dated Aug. 15, 2014.

METHOD AND SYSTEM FOR LIQUID CHROMATOGRAPHY FLUIDIC MONITORING

CROSS-REFERENCE TO RELATED APPLICATIONS

This application is the United States National Stage Application, under 35 USC 371, of International Application No, PCT/US2012/034895 having an international filing date of Apr. 25, 2012 and designating the United States which claims the benefit of the filing date, under 35 USC 365(c) and 35 USC 120, of International Application No. PCT/US2011/058230 having an international filing date of Oct. 28, 2011 and designating the United States, which claims the benefit of the filing date, under 35 USC 119(e), of U.S. Provisional Application 61/408,046 filed on Oct. 29, 2010, all said applications incorporated by reference herein in their entireties.

TECHNICAL FIELD

This invention generally relates to chromatography, and more particularly to an automated apparatus and method for monitoring the correctness of the installation and placement of solvents, mobile phases or other reagents within a chromatograph instrument or system.

BACKGROUND ART

Liquid chromatography (LC) is well-known in the fields of chemical separation, compound purification and chemical analysis. A liquid chromatograph generally includes a separation column that comprises a capillary tube that is packed with a permeable solid material that either is, itself, a chromatographic stationary phase or otherwise comprises or supports a chromatographic stationary phase. A mobile phase, which is a fluid mixture comprising a compound of interest for purification or separation as well as one or more solvents, is caused to flow through the column under pressure from an input end to an output end. Generally, the chemical properties of the stationary phase and the mobile phase solvents are such that the degree of partitioning of the compound of interest between the mobile phase and the stationary phase is different from the degree of partitioning of other compounds within the fluid. As a result, the degree of retention or time of retention of the compound of interest within the column is different from the degree or time of retention of the other compounds, thus causing a physical separation or at least partial purification of the compound of interest from the other compounds.

There are numerous solvents available for liquid chromatography. For instance, the HPLC solvents available under the Fluka® brand name from Sigma-Aldrich Corporation (3050 Spruce Street, St. Louis, Mo. 63103 USA) include: water, Acetonitrile, Benzene, 1-Butanol, 2-Butoxyethanol, tert-Butyl methyl ether, Carbon tetrachloride, 1-Chlorobutane, Chloroform, 2-Chloropropane, Cyclohexane, Cyclopentane, 1,2-Dichloroethane, Dichloromethane, Diethyl ether, 1,2-Dimethoxyethane, N,N-Dimethylacetamide, Dioxane, Ethanol, Ethanol, Ethyl acetate, Heptane, Hexane, Isooctane, Methanol, Methanol, Methyl acetate, Nitromethane, Pentane, 1-Propanol, 2-Propanol, 2-Propanol, Tetrachloroethylene, Tetrahydrofuran, and Toluene.

Within a chromatograph instrument or system, solvents or other reagents are generally made available to the various columns, pumps, valves and associated interconnecting tubing lines by means of a dedicated rack or compartment. The rack or compartment generally comprises a dedicated storage area for the set of solvents or other reagents that will routinely be needed or that may be needed by the chromatograph instrument or system during the course of several separations. The reagent rack is generally designed to be accessed by an operator or technician at such times that one or more solvents or reagents need to be replaced, having been depleted over the course of operation of the instrument or system.

Successful chromatographic separations depend on specific chemical interactions of the various analytes and other components with a stationary phase and with the various chemical constituents of a mobile phase. Because different analytes have different respective chemical properties, it is important that the correct set of solvents or reagents for an analysis at hand are mixed with a sample containing or potentially containing any particular analyte. Therefore, the various different solvents or reagents are provided in respective dedicated bottles or other containers within a reagent or solvent rack or compartment. The different containers or bottles either have respective assigned locations within the rack or compartment or are associated with different respective assigned draw tubes for aspiration of the solvent or reagent into the system.

Because of the specificity of solvents or other reagents required for any particular chromatographic analysis protocol, it is important that these materials are not confused with one another (or with completely different substances) or misplaced within a reagent or solvent rack or compartment. Although reagents, solvents and other required chemicals are generally supplied by manufacturers in well-labeled containers, these materials may be re-distributed into smaller containers within a laboratory environment. The smaller containers may be multi-purpose, initially-unlabeled vessels which require appropriate manual labeling upon initial receipt of material transferred from a manufacturer's original container. The manual label applied in a laboratory may be a non-permanent label. After manual labeling, the small transfer vessel may be handled within the laboratory many times and by many different users, since multiple replenishments from a large-volume manufacturer's "bulk" container may be required as the material within the vessel is routinely consumed. The same vessel may be re-inserted into a solvent or reagent rack many times.

Many opportunities for operator error will occur over the course of the multiple handlings of the transfer vessel or, occasionally, even a manufacturer's original container. For instance, a temporary label may be lost and replaced with an incorrect label. Even if the label is correct, the operator may transfer the wrong material into the transfer vessel. Even if the label and material are correct, the operator may misplace the vessel within a reagent rack or compartment. Conventional chromatograph systems are designed to expect that particular solvents or reagents will be drawn into particular respective tubing lines. If an incorrect material is supplied, through any one or more of the errors listed above, the chromatograph will continue to perform the pre-programmed steps of an analysis protocol with the wrong material. This may lead to incorrect or poor-quality results, necessitating repetition of many faulty analyses. In a worst-case scenario, the error may never be discovered, and inappropriate actions may be taken based on the incorrect analytical results. Nonetheless, by comparing the properties of a solvent—such as viscosity and compressibility—with the expected values which can be obtained through user input or by means of a sensor mechanism, such as bar code, the solvent identity can be validated. Accordingly, there is a need in the art for an automated chromatograph system that can take automated procedural steps in an attempt to recognize unexpected solvents or reagents before analysis steps are performed unexpected material and that can raise an operator alert if any such errors are detected.

Liquid chromatography systems utilized in clinical laboratories or for purposes of drug discovery may remain in near continuous operation over long periods of time. As a result of wear, repeated handling, repeated pressurization, multiple replacements of samples, etc., occasional or periodic situations or conditions may occur which result in sub-optimal performance of or even instrumental malfunctions in chromatographic systems. For example, as a result of long term repeated pressurization of fluid lines and other fluidic components, leaks may develop which either lead to undesirable loss of fluids from a fluidic system or, perhaps, undesirable ingestion of air into the system. Repeated replacement of sample vials or fluid or solvent containers may lead to contamination of fluid lines by particulates or ingested air. Further, since many components such as pumps and valves undergo repeated mechanical operation, long term wear of such components may occur which, if not addressed, may lead to loss of precision, loss or pressure integrity or even total malfunction of one or more components. Finally, undesirable pressure imbalances may occur within fluidic systems comprising various fluidic sub-systems, each sub-system having its own respective pumps. Accordingly, there are needs in the art for methods for monitoring the performance of chromatographic systems for the purpose of detecting sub-optimal conditions, deterioration of performance, possible future failures, etc. and for warning users of the need to take corrective action or notifying users of estimated remaining useful lifetimes of components. Moreover, there is a need in the art for an automated chromatograph system that can perform such monitoring and provide such warnings or notifications automatically. Preferably, liquid chromatograph (LC) system self-diagnostics and monitoring should include self-diagnoses, validation and troubleshooting of i) the pump and ii) the LC system plumbing for leakage, air bubbles and fluid pathway blocking.

There is also a need in the art for methods for balancing pressures between different fluidic sub-systems. The compressibility of an LC solvent affects the flow rate which in turn affects the chromatographic performance. This effect is an issue for all high-performance (or high-pressure) liquid chromatography (HPLC) systems in general and for those that use syringe pumps in particular. This effect is one of the main drawbacks associated with the syringe type of pump, although such syringe pumps provide other advantages such as smooth gradients and a high degree of robustness. M. Martein, et. al ("The use of syringe-type of pumps in liquid chromatography in order to achieve a constant flow-rate", Journal of Chromatography, 112, 1975) concluded that "[i]t is therefore not surprising that the syringe-type pumps have evolved into very sophisticated and expensive devices" in order to compensate the compressibility issue. Even so "the use of syringe-type pumps is often more difficult and less satisfactory than the use of other types of pumps."

DISCLOSURE OF INVENTION

The present disclosure addresses the above-noted needs in the conventional art through the teaching of methods and systems for monitoring properties of fluids provided to liquid chromatography systems and comparing the monitored properties to the values that are expected if correct fluids are provided. Such methods and systems are also capable of monitoring the leak-tight worthiness of pumps and other mechanical or fluid-containing components of the liquid chromatography systems.

The present teachings address the issue of the sensitivity of syringe-pump systems to liquid compressibility in at least two ways. First, a general-purpose compressibility compensation algorithm can be applied. The algorithm can compare the compressibility of a solvent in a compressed volume within a specific time with the known compressibility of the expected solvent. Then, an actual flow rate can be obtained to take account of the effect of the compressibility. The expected flow rate can be set as a target for the pump to achieve. This method eliminates the need of the extra flow rate sensors. A controller such as PID (proportional-integral-derivative) can be used to achieve the target flow rate.

Secondly, the various scenarios exhibiting the most serious effects of compressibility are addressed individually. Three different problematic scenarios are investigated: i). a pump undergoing connection to a pressurized fluid pathway, ii) the achievement of flow rate with pressure and iii) situations in which different fluid pathway/subsystems possibly having different pressures are interconnected or disconnected from one another during the operation of a liquid chromatograph. In the first such scenario, the pressurized fluid pathway might flow back to the unpressurized pump to compress the fluid inside the pump, thereby causing a sudden pressure drop and unintended solvent mixing. In the second scenario, the flow rate with pressure takes time to reach the pressure equilibrium and to reach the specified flow rate as a result of the compressibility of the solvent. The time taken to reach the equilibrium is determined by the compressibility of the solvent, the pressure, the flow rate and the solvent. The equilibration time could range from several seconds to more than hours. In the third scenario, the pressure imbalance could cause sudden unintended large fluid flow from a high-pressure subsystem to a low-pressurize sub-system. Even with a one-way fluid component such as check valve to prevent backflow, the low-pressure subsystem needs time to reach pressure equilibrium with the high pressure subsystem. The consequent difference between the actual and expected flow rates as a result of the compressibility is so large as to dramatically affect the performance of the liquid chromatograph.

By addressing each of the above scenarios individually, an optimized simple algorithm can be developed to only solve the problem associated with the particular scenario. This targeted approach can achieve the best performance, in contrast to employing a generalized algorithm. If a generalized method is used for all these scenarios, then the best performance is difficult to achieve and the method could be very complicated.

In accordance with a first aspect of the present teachings, there is disclosed a system for providing a solvent or reagent to a liquid chromatography system comprising: a valve comprising a common port and a plurality of other ports, configurable such that the common port may be fluidically coupled to any one of the other ports; a pump fluidically coupled to the common port of the valve; a plug configured to block flow through a first one of said other ports of the valve; a container containing the solvent or reagent, said container fluidically coupled to a second one of said other ports of the valve; and a pressure gauge or sensor configured to measure fluid pressure within the pump, wherein the solvent or reagent is provided to the liquid chromatography system by a fourth one of the other ports. The pumps may comprise syringe pumps. The system may further comprise a fluid tubing line having a known resistance to fluid flow fluidically coupled to a third one of said other ports of the valve. Alternatively, the system may further comprise a fluid resistance such as a fluid tubing line, a column, etc., wherein the fluid resistance could be either known or unknown as long as it is constant. The system may further comprise a computer or electronic controller electrically or electronically coupled to the pump, the pressure gauge or sensor and the valve. The system may still further comprise an electronically-readable medium having thereon program instructions readable by the computer or electronic controller, said instructions operable to cause the computer or electronic controller to measure readings of the pressure gauge or sensor while causing the pump to apply a force to a fluid therein so as to urge said fluid to either the first or third port of the valve.

In accordance with a second aspect of the present teachings, there is disclosed a method for monitoring fluids within a liquid chromatography system comprising: (a) configuring a valve so as to draw a fluid from a container into a pump; (b) configuring the valve so as to fluidically couple the pump to a port of the valve that is coupled to a plug that prevents fluid flow through said port; (c) causing the pump to progressively compress the fluid therein, while measuring a pressure of the fluid in the pump; and (d) determining if a rate of increase of the measured pressure substantially matches an expected value. Additional steps of the method may comprise one or more of: (e) upon measuring a maximum pressure or, alternatively, any suitable pre-determined pressure, maintaining a piston of the pump in a constant position for a time of pre-determined length while continuing to measure the pressure of the fluid in the pump; and (f) determining if a decrease of the measured pressure by more than an acceptable value occurred during the time period. Still further steps of the method may comprise: (g) causing the pump to relieve the pressure of the fluid in the pump; (h) configuring the valve so as to fluidically couple the pump to a fluid pathway having a pre-determined resistance to fluid flow therethrough; (i) causing the pump to displace fluid into fluid pathway at a set flow rate while measuring the pressure of the fluid in the pump; and (j) determining if an increase of the measured pressure during the fluid displacement substantially matches a second expected value. The method may include raising an alarm either that the fluid in the container may not match expectations or that the pump may not be leak-free according to expectations depending on the measured increases or decreases in the pressure of the fluid in the pump.

In accordance with a third aspect of the present teachings, there is disclosed a liquid chromatography system comprising: (a) a valve system or fluid selecting apparatus having an output port and a plurality of input ports thereof, each of the plurality of input ports fluidically coupled to a respective fluid-providing sub-system, each fluid-providing sub-system comprising: (i) a valve comprising a common port and a plurality of other ports, configurable such that the common port may be fluidically coupled to any one of the other ports; (ii) a pump fluidically coupled to the common port of the valve; (iii) a plug configured to block flow through a first one of said other ports of the valve; (iv) a container containing a fluid, said container fluidically coupled to a second one of said other ports of the valve; (v) a pressure gauge or sensor configured to measure fluid pressure within the pump; and (vi) a third one of the other ports fluidically coupled to the valve system or fluid selecting apparatus; (b) a chromatograph column having a first end fluidically coupled to the output of the valve system or fluid selecting apparatus and a second end; and (c) a detector fluidically coupled to the second end of the chromatograph column. At least one fluid-providing sub-system may further comprise (vii) a fluid tubing line having a known resistance to fluid flow fluidically coupled to a fourth one of the other ports of the valve of the respective fluid-providing sub-system.

In accordance with a fourth aspect of the present teachings, there is disclosed a method for monitoring a fluidic system of a liquid chromatography system, wherein the system comprises a valve, a container having a known fluid therein and a syringe pump having a piston, and wherein the syringe pump is fluidically coupled to the valve. According to this aspect, the method is characterized by: (a) drawing the fluid from the container into the syringe pump; (b) configuring the valve so as to fluidically couple the pump to a port of the valve that is coupled to either a fluidic pathway through the fluidic system or to a plug that prevents fluid flow through said port; (c) causing the piston of the syringe pump to move at a predetermined rate in a direction so as to progressively compress the fluid therein or expel the fluid to the fluidic pathway, while measuring a pressure of the fluid; (d) determining a profile of the variation of the measured pressure for the time that the piston is caused to move; (e) comparing the determined profile to an expected profile that depends upon the fluid; and (f) providing a notification of a sub-optimal operating condition or malfunction if the determined profile varies from the expected profile by greater than a predetermined tolerance. In some instances, an expected profile may be reduced to simply one or more characteristic rates of change of pressure, such as a rate of pressure increase or a rate of pressure decrease.

In various embodiments, the step (b) of configuring the valve may comprise configuring the valve so as to fluidically couple the pump to a port of the valve that is coupled to a fluidic pathway having an intentional flow blockage therein that prevents flow through the fluidic system beyond the intentional flow blockage. Such an intentional flow blockage may comprise one or more closed valves or may be provided at a nominal position of a chromatographic column within the fluidic system. In some embodiments, the intentional flow blockage is provided in a cartridge that is interchangeable with and that is disposed within the fluidic system at the nominal position of a two-column-bearing cartridge.

In various embodiments, the step (b) comprises configuring the valve so as to fluidically couple the pump to a port of the valve that is coupled to a fluidic pathway that includes a length of empty tubing that replaces a chromatographic column at the nominal column position and the step (0 comprises providing a notification that the fluid pathway is blocked if the determined pressure profile includes a pressure increase that exceeds an expected increase in pressure by greater than the predetermined tolerance. In various other embodiments, the step (b) of configuring the valve comprises configuring the valve so as to fluidically couple the pump to a port of the valve that is coupled to a fluidic pathway having a known resistance to fluid flow, and the step (e) of comparing the determined profile to an expected profile comprises comparing the determined profile to an oscillatory profile, the oscillations of said profile relating to mechanical movement within the syringe pump.

In various embodiments, the step (0 of providing a notification may comprise providing a notification that an air or gas bubble is present within the fluidic system if the determined pressure profile includes a delay in an increase in pressure, relative to the expected profile. Various embodiments of the method may include the additional steps of (g)

causing the piston of the syringe pump to remain in a fixed position, while measuring a pressure of the fluid; (h) determining a rate of decrease of the measured pressure while the piston is in the fixed position; (i) comparing the determined rate of pressure decrease to a model relating rate of pressure decrease to remaining pump lifetime; and (j) either providing a prediction of remaining pump lifetime or providing a warning that the pump should be replaced or serviced based on the comparing.

In accordance with a fifth aspect of the present teachings, there is disclosed a method of balancing fluid pressure between a first portion and a second portion of a fluidic system of a liquid chromatography system, wherein the second portion is initially at higher fluid pressure than the second portion, wherein the liquid chromatography system comprises a coupling system that may either fluidically interconnect or mutually isolate the first and second fluidic system portions, and wherein the liquid chromatography system further comprises a first syringe pump, a selection valve that is fluidically coupled to the first syringe pump and to the first portion of the fluidic system, a second syringe pump that is fluidically coupled to the second portion of the fluidic system, a first pressure sensor configured to measure pressure within the first syringe pump and a second pressure sensor configured to measure pressure within the fluidic system. According to this aspect, the method is characterized by: (a) configuring the selection valve so as to fluidically couple the first syringe pump to a port of the valve that is coupled to a plug that prevents fluid flow through said port; (b) compressing a fluid within the first syringe pump so that a reading of the first pressure sensor matches a reading of the second pressure sensor; (c) configuring the selection valve so as to fluidically couple the first syringe pump to a port of the valve that is coupled to the first portion of the fluidic system; and (d) fluidically interconnecting the first and second portions of the fluidic system using the coupling system.

In various embodiments, the first portion of the fluidic system includes a first chromatographic column and the second portion of the fluidic system includes a second chromatographic column. The coupling system may comprise a one-way check valve disposed within the first portion of the fluidic system and a mixing tee coupler at which fluids from the first and second portions are mixed. Alternatively, the fluid coupling may comprise the one-way check and a multiple-port rotary valve, wherein fluids from the first and second portions may be mixed. In some embodiments, the first portion of the fluidic system comprises a chromatography column-loading sub-system and the second portion of the fluidic system comprises an eluting sub-system.

In accordance with another aspect of the present teachings, there is disclosed a method of operating a liquid chromatography system, wherein the system includes a chromatographic column having a nominal operating pressure, a syringe pump, a pressure sensor configured to measure pressure within the syringe pump, and a selection valve that is fluidically coupled between the syringe pump and the chromatographic column. According to this aspect, the method is characterized by: (a) configuring the selection valve so as to fluidically couple the first syringe pump to a port of the valve that is coupled to a plug that prevents fluid flow through said port; (b) compressing a fluid within the syringe pump until a reading of the pressure sensor matches the nominal operating pressure; (c) configuring the selection valve so as to fluidically couple the syringe pump to a port of the valve that is coupled to the chromatographic column; and (d) operating the syringe pump so as to pump a sample fluid through the chromatographic column.

In accordance with yet another aspect of the present teachings, there is disclosed a method for monitoring for the existence of leaks within a fluidic system of a liquid chromatography system, wherein the liquid chromatography system comprises a valve, a container having a known fluid therein, a syringe pump having a piston, and a pressure sensor wherein the syringe pump is fluidically coupled to the valve. According to this aspect, the method is characterized by: (a) drawing the fluid from the container into the syringe pump; (b) configuring the valve so as to fluidically couple the pump to a port of the valve that is coupled to either a fluidic pathway of the fluidic system having an intentional flow blockage therein or to a plug that prevents fluid flow through said port; (c) causing the piston of the syringe pump to move at a predetermined rate in a direction so as to increase the pressure of the fluid therein or within the fluidic pathway; (d) causing the piston of the syringe pump to remain in a fixed position, while measuring a pressure of the fluid; (e) determining a rate of decrease of the measured pressure while the piston is in the fixed position; and (f) providing a warning that a leak is present if the determined rate of pressure decrease exceeds a pre-determined threshold value. In some embodiments, the intentional flow blockage may be provided at a nominal position of a chromatographic column within the fluidic system. In some embodiments, the intentional flow blockage is provided in a cartridge that is interchangeable with and that is disposed within the fluidic system at the nominal position of a two-column-bearing cartridge. In various embodiments in which the valve is configured to fluidically couple the pump to the plug, the determined rate of pressure decrease may be compared to a model relating rate of pressure decrease to remaining pump lifetime; and a prediction of remaining pump lifetime may be made based on the comparing.

BRIEF DESCRIPTION OF DRAWINGS

The above noted and various other aspects of the present invention will become apparent from the following description which is given by way of example only and with reference to the accompanying drawings, not drawn to scale, in which.

MODES FOR CARRYING OUT THE INVENTION

The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. To appreciate the features of the present invention in greater detail, please refer to FIGS. 1-17 in conjunction with the following discussion.

Figure 1:
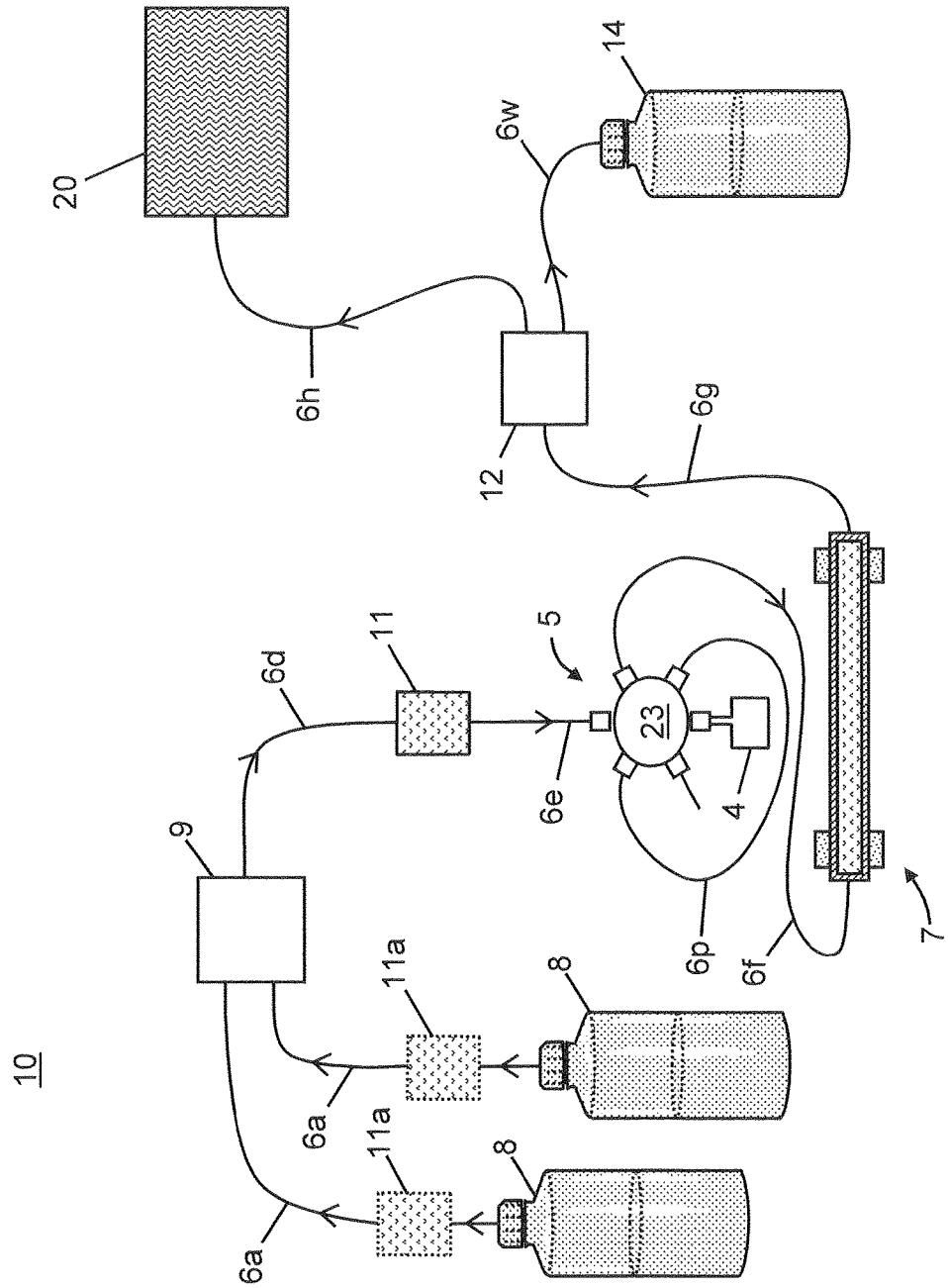
FIG. 1 is a schematic illustration of a generalized conventional liquid chromatography-mass (LCMS) spectrometry system.

FIG. 1 is a schematic illustration of a conventional liquid chromatography (LC) system. The system 10 shown in FIG. 1 comprises a chromatograph column 7 for separating a liquid chemical mixture into its constituent substances and a detector 20 (such as spectrophotometer or a mass spectrometer) fluidically coupled to the column 7 for detecting or identifying some or all of the separated constituent substances as they are received, in sequence from the column 7. The column receives a fluid stream comprising one or more selected solvent fluids or reagents supplied from containers 8 as well as a sample of interest from sample source 4. The various different solvent or reagent fluids, which may comprise a chromatographic mobile phase, are delivered along fluid tubing lines 6a to valve or fluid selecting or mixing apparatus 9 which may mix the fluids or select a particular fluid. As illustrated, the apparatus 9 is a three-way valve but may comprise a more complex valve or valve system if more than two different solvent fluids are provided. Alternatively, the apparatus 9 could comprise a simple mixing junction or mixing chamber.

The fluids are drawn into the system 10 and propelled to the chromatographic column 7 therein by means of a pump 11 that is fluidically coupled to the output of the valve or fluid selecting apparatus 9 by fluid tubing line 6d. Alternatively, the single illustrated fluid pump 11 could be replaced separate pumps—one for each solvent or reagent—disposed at positions 11a in fluid tubing lines 6a. The fluids output from the pump or pumps are delivered to a sample injector apparatus 5 along fluid tubing line 6e and are mixed together with a sample provided from the sample source 4. The sample injector apparatus 5 may comprise, in a well-known fashion, a multiple-port rotary valve 23 and an injection loop 6p fluidically coupled between two of the ports.

An input of the column 7 of system 10 is fluidically coupled to and receives a mixture of sample and solvent fluids from an output port of the sample injector apparatus 5 by fluid tubing line 6f. Differential partitioning of the various chemical constituents of the mixture between the mobile phase and a stationary phase packed within the column leads to differential retention of the various constituents within the column and consequent different respective times of elution of the constituents from the column output to fluid tubing line 6g. An optional valve 12 may separate the eluting substances, either continuously or at various times, into a portion that is delivered to waste container 14 along fluid tubing line 6w and an analysis portion that is delivered the detector 20 along fluid tubing line 6h.

Figure 2:
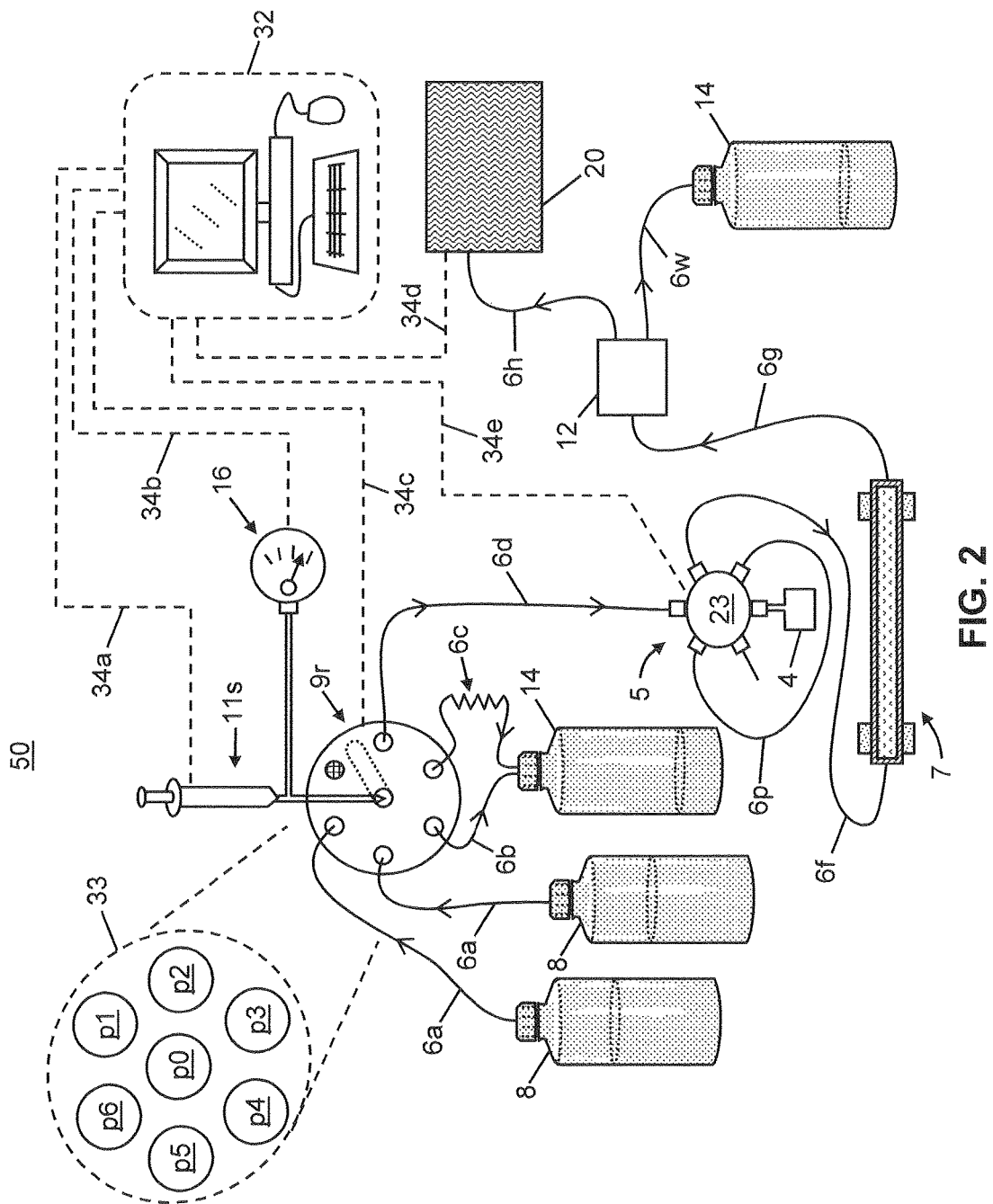
FIG. 2 is a schematic illustration of an LCMS system in accordance with the present teachings.

The conventional system 10 shown in FIG. 1 is susceptible to the possible handling errors of a transfer vessel or, occasionally, even a manufacturer's original container, as described supra herein. Accordingly, FIG. 2 provides a schematic illustration of an improved LCMS system, system 50, in accordance with the present teachings. In the system 50, the solvents or reagents that are drawn from containers 8 into the fluid tubing lines 6a are delivered to a multiple-port source valve 9r.

Figure 3:
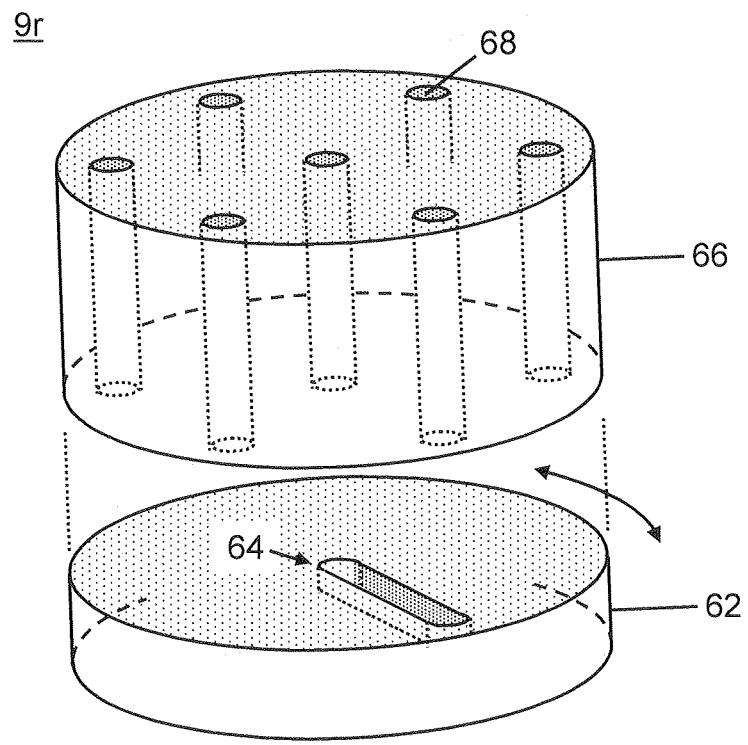
FIG. 3 is an illustration of an exemplary rotary valve assembly as may be employed within an apparatus in accordance with the present teachings.

As indicated in the inset 33 of FIG. 2, the source valve 9r comprises a common port p0 as well as several dedicated ports—in the illustrated system, six dedicated ports denoted as ports p1-p6. The source valve 9r may comprise a type of a known multiple-port rotary valve, such as the valves known as Rheodyne valves sold by IDEX Health & Science, 619 Oak Street Oak Harbor, Wash. USA. A more-detailed illustration of an exemplary source valve 9r is shown in FIG. 3. The source valve 9r shown in FIG. 3 comprises, in known fashion, a stator portion 66 having a plurality of fluid passages 68 therein passing through the stator portion from one end to another end and a rotor portion 62 having a groove or channel 64 on a side facing the stator portion. As shown, the stator comprises a central fluid passage (corresponding to the port p0 shown in FIG. 2) as well as six peripheral fluid passages (corresponding to the ports p1-p6 shown in FIG. 2) radially disposed about the central passage. The rotor portion 62 may rotate, as illustrated by the double-headed arrow in FIG. 3, so that any one of the peripheral passages may be fluidically connected to the central passage, within the source valve 9r, by means of the groove or channel 64. Although a rotary valve is shown, the invention is not intended to be limited to such, as the rotary valve is but one example of a valve which may be employed.

Returning to FIG. 2, the solvents or reagents are drawn from their respective containers 8 into and through the source valve 9r by means of a syringe pump 11s which is coupled to the central or common port p0 as well as to a pressure sensor or gauge 16. Two different solvent or reagent fluids may be fluidically coupled to two respective ports, for example, ports p5 and p6, of the source valve 9r by means of the fluid tubing lines 6a. To draw either one of these fluids into the cylinder of the syringe pump, the source valve is configured such that the central port p0 is fluidically coupled to one of ports p5 and p6 while a piston of the syringe pump is withdrawn.

A computer or other electronic logic controller 32 may be included within the system 50 so as to receive information from and transmit control signals to various components of the system. The computer or other electronic logic controller 32 may be electronically coupled to the pump 11s, the pressure sensor or gauge 16 and the source valve 9r by means of electronic communication lines 34a, 34b and 34c, respectively. The computer or other electronic logic controller 32 may also be electronically coupled to other components of the system 50, although such couplings are not explicitly illustrated in FIG. 2.

One port, for example, port p1 of the source valve is blocked or plugged so that fluid cannot exit through this port and may be a default position of the source valve when the pump is not in use. If the source valve is configured to dispense solvent to port p1 and force is applied to the syringe pump piston, the pressure measured by sensor or gauge 16 is expected to rise rapidly. In the absence of a leak, the rate of pressure rise depends on fluid compressibility. The rate of pressure rise may be used to verify the correctness of a particular solvent or reagent, from among a limited number of choices. The use of the plug position p1 as a source valve "output" can also be used to verify pump seal performance and pump priming. Using a calibration fluid of known compressibility, a failure of the pressure to increase as expected or an unexpected pressure decrease can indicate an apparatus defect.

Another port, for instance, port p2 of the source valve 9r is the output to the sample injector apparatus 5 via fluid tubing line 6d. Another port, for instance, port p3 is used to output a small portion of a previously aspirated solvent into a waste container through a calibrated length of resistive tubing 6c. The tubing 6c may comprise a restricted-diameter inner bore which provides a known resistance to fluid flow. If the source valve is configured to dispense solvent to port p3 and force is applied to the syringe pump piston, the solvent will be dispensed to the waste container 14 concurrent with a rise in pressure, as measured by sensor or gauge 16, that corresponds to solvent viscosity. This measured pressure rise may be used to verify solvent identity, from among a limited number of choices. The relation between pressure rise and viscosity may be calibrated by dispensing a calibration fluid having known viscosity through port p3. Finally, another port, such as port p4, is an output to the waste container 14, using least resistance (e.g. regular) fluid tubing line 6b, which is used for pump prime and purge operations.

With regards to the system 50 shown in FIG. 2, it is to be kept in mind that the system may be expanded by including additional instances of the sub-set of components comprising: the one or more solvent or reagent containers 8, the source valve 9r having a plugged port, the pump 11s, the pressure sensor or gauge 16, the known-resistance tubing 6c, the waste container 14 and the other connecting fluid tubing lines 6a, 6b and 6d. This sub-set of components may be considered to comprise a fluid-providing sub-system of the liquid chromatograph system 50. Alternatively or in addition, different respective solvents may be provided in different respective instances of said fluid-providing sub-system, especially if a large number of solvents or reagents are provided within the system.

Many liquid chromatography systems employ more than one chromatographic column during fractionation, separation or purification of an analyte. For instance a first column may comprise a sample "cleanup" column and a second column may comprise an analytical column. The cleanup column, according to some embodiments, may be a size exclusion or affinity liquid chromatography column or a High-Turbulence Liquid Chromatography column used for matrix interference removal. For instance, a test sample may applied to a first column (e.g., a clean-up column such as a Cyclone P column or the like) at the inlet port, eluted with a solvent or solvent mixture onto a second column (e.g., an analytical column such as a Hypersil Gold PFP or the like), and eluted with a solvent or solvent mixture from the second column to the outlet port. Different solvent modes may be selected for eluting the analytes. For example, liquid chromatography may be performed using a gradient mode, an isocratic mode, or a polytyptic (i.e. mixed) mode.

Figure 4A:
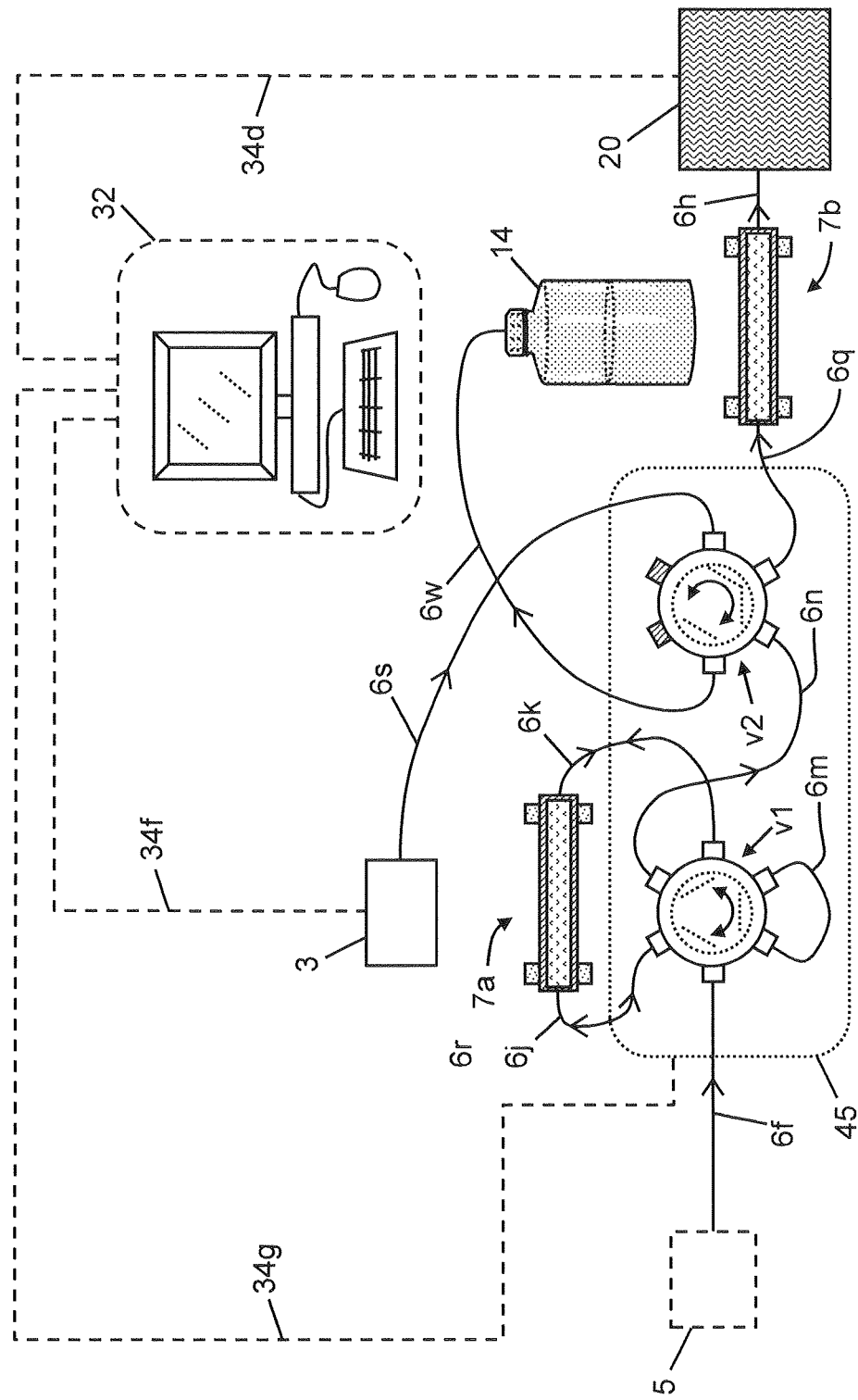
FIG. 4A is a schematic diagram of an exemplary two column LCMS system employing a fluid monitoring portion in accordance with the present teachings.
Figure 4B:
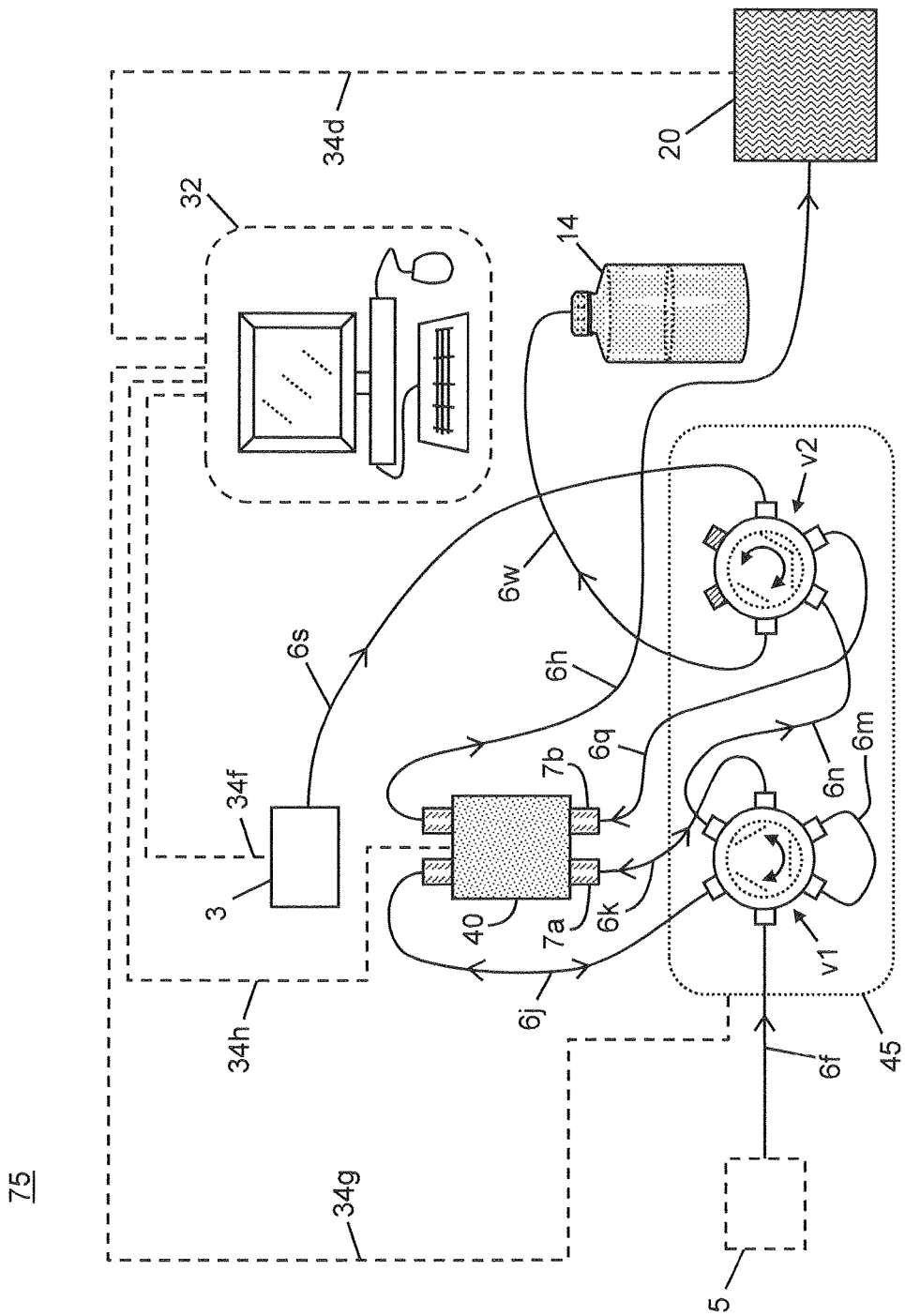
FIG. 4B is a schematic diagram of a second exemplary two column LCMS system employing a fluid monitoring portion in accordance with the present teachings.

FIGS. 4A and 4B are schematic diagrams of two exemplary two-column LCMS systems employing a fluid monitoring portion in accordance with the present teachings. Sample injector 5 and fluid tubing line 6f are reproduced from FIG. 2. For clarity of presentation, components upstream of the sample injector (including the solvent or reagent containers 8, the source valve 9r, the pump 11s, the pressure sensor or gauge 16, the known-resistance tubing 6c, the waste container 14, the connecting fluid tubing lines 6a, 6b and 6d and the electronic communication lines 34a, 34b and 34c) are not shown but are considered to be present in the systems shown in FIGS. 4A-4B. Alternatively, the sample injector 5 shown in FIGS. 4A-4B may be replaced by a more-complex sample source sub-system—possibly comprising multiple sample injectors, pumps, valves, mixing tee joints, solvent or reagent containers, and tubing lines. In both the system 70 (FIG. 4A) and the system 75 (FIG. 4B), two chromatograph columns—a first column 7a and a second column 7b—are utilized. The first column 7a may advantageously comprise a cleanup column that may be employed to separate certain classes or sub-sets of compounds from one another (e.g. large molecule versus small molecule, or polar versus non polar) with the fraction that may contain possible analyte substances retained and the other fraction discarded (or vice versa). The second column, column 7b, is an analytical column that may be similar to the single column 7 of the system 50 (FIG. 2). The retained fraction eluted from the first, cleanup column 7a may be separated into particular isolated compounds by the second column 7b. The eluted constituents may be provided to detector 20 along fluid tubing line 6h.

As an example of a two-stage chromatographic separation, a TurboFlow® column (also known as a High Turbulance Liquid Chromatography or HTLC column) may be employed as the cleanup column 7a in a first separation step in order to isolate and possibly concentrate a subset of compounds based on their size range or molecular weight range (or some other property). TurboFlow® methods and apparatus are described in detail in U.S. Pat. Nos. 5,772,874; 5,919,368 and 6,149,816, all of which are hereby incorporated by reference in their entirety as if fully set forth herein. Briefly stated, the TurboFlow® apparatus and methods include or relate to a chromatography column or body that is formed as a substantially uniformly distributed multiplicity of rigid, solid, porous particles having substantially uniform mean cross-section dimensions or diameters of not less than about 30 µm, typically 50 µm or greater up to, but not limited to, 1000 µm in certain instances. The particles are selected from a range of various sizes and shapes and are held together in a body or column as by pressure, sintering and the like so that interstitial channels having a total interstitial volume of not less than about 45% of the total volume of the column are formed between the particles. The surfaces of the particles, including the inner surfaces of the pores in the particles, are chromatographically active, as by being coated with chromatographic stationary phase layers.

Because of the nature of the particles and packing in a TurboFlow® column, the flow of the fluid mixture through the column can be at a high flow rate and is believed that, under such conditions, turbulent flow of the mixture is induced within at least a major portion of the interstitial volume, and it is postulated that such turbulent flow in fact enhances the rate of mass transfer, thus increasing the dynamic capacity of the column. From the principles of turbulence, diffusion, and chemistry, small sample molecules may be separated from a sample matrix in a Turbo-Flow® column. Since small molecular weight molecules diffuse faster than large molecular weight molecules, the small sample compounds diffuse into the particle pores. The turbulent flow of the mobile phase quickly flushes the large sample compounds through the column to waste before they have an opportunity to diffuse into the particle pores. Of the sample molecules that enter the pores, those that have an affinity to the chemistry inside the pores bind to the internal surface of the column particles. The small sample molecules that have a lower binding affinity quickly diffuse out of the pores and are flushed to waste. A change in mobile phase, temperature or other parameter may then cause those molecules that were bound by the TurboFlow® column to elute to the analytical column for further separation.

The flow of analyte bearing or other fluids—including samples, solvents and mixtures thereof possibly together with other chemical components—through the two chromatograph columns 7a, 7b of either the system 70 or the system 75 is controlled by two multi-port valves v1, v2, illustrated as valve system 45. Each valve may be a rotary valve of a known type, such as Rheodyne valves in which a rotor portion comprises two or three channels that may fluidically interconnect various pairs of adjacent ports, depending on the orientation of the rotor portion. The rotation and channels are schematically indicated, respectively, by a double-headed arrow and by a set of dotted straight lines in each of the valves v1 and v2. The first valve v1 may be configured to as to fluidically interconnect the members of three different pairs of adjacent ports; the second valve may be configured so as to fluidically interconnect a first pair of adjacent ports as well as all the ports of a triplet of ports, as shown by the dotted line.

One port of the first valve v1 receives a fluid from fluid tubing line 6f. Fluid tubing lines 6j and 6k fluidically connect the ports of the first column 7a to respective ports of the first valve; fluid tubing line 6n fluidically connects a port of the first valve v1 to a port of the second valve v2 and another fluid tubing line 6m fluidically interconnects two ports of the first valve. The first valve v1 and associated fluid tubing lines may be configured (as shown) such that fluid may be caused to flow through the first column 7a in either direction.

In either the system 70 or the system 75, a port of the second valve receives a fluid, possibly comprising various solvents or other chemical constituents or mixtures thereof, from a solvent source 3 via fluid tubing line 6s. The solvent source 3 may comprise a sub-system including various reagent containers as well as one or more syringe pumps, rotary source valves, pressure sensors, resistive fluid tubing lines, mixing tee joints, waste containers and other interconnecting fluid tubing lines similar to corresponding features illustrated in FIG. 2. Thus, the solvent source 3 may include a second parallel instance of a fluid-providing sub-system as described with reference to the system 50 or may comprise a more-complex fluid-providing sub-system. One or more electronic communication lines 34f may electronically couple various of the components of the solvent source 3 to the computer or other electronic logic controller 32 in similar fashion as shown in FIG. 2.

Two ports of the second valve v2 may be plugged or otherwise unused, as indicated by hatch marks in FIGS. 4A, 4B. Another port of valve v2 directs non-analyzed fluids to a waste container 14 along fluid tubing line 6w. A final port of the valve v2 is fluidically coupled to an inlet port of the second chromatograph column 7b via fluid tubing line 6q. One or more electronic communication lines 34g may couple the computer or other electronic logic controller 32 to the valves v1, v2 so as to control their operation.

The system 75 illustrated in FIG. 4B is similar to the system 70 illustrated in FIG. 4A with the exception that the two chromatograph columns 7a, 7b are housed together in a cartridge or housing 40. An example of a two-column cartridge that may be employed as the cartridge 40 is disclosed in a co-pending International (PCT) Application filed on Oct. 28, 2011 titled "Modular Multiple-Column Chromatography Cartridge"; International Application No. PCT/US11/58229) and assigned to the assignee of the present invention and incorporated herein by reference in its entirety. The cartridge 40 may include, in addition to a housing, a computer-readable identification (an indicator or identifier), such as a barcode or an RFID tag and may also include on-board computer readable memory, such as flash memory or any other form of electronic memory device, as well as an on-board electronic processor. The on-board memory, if present, may be used to store data relating to the use of the columns of the cartridge, such as supported chromatographic methods or column usage history. Further, the cartridge 40 may include one or more heaters to maintain one or the other of the columns at a temperature corresponding to an analysis protocol, as well as one or more sensors of temperature or some other physical quantity. Accordingly, the cartridge may be electronically coupled to the computer or other electronic logic controller 32 by an electronic communication line 34h so as to, for instance, transfer identification or other data to or from a memory unit of the cartridge, to control heaters or to monitor the sensors.

Figure 5:
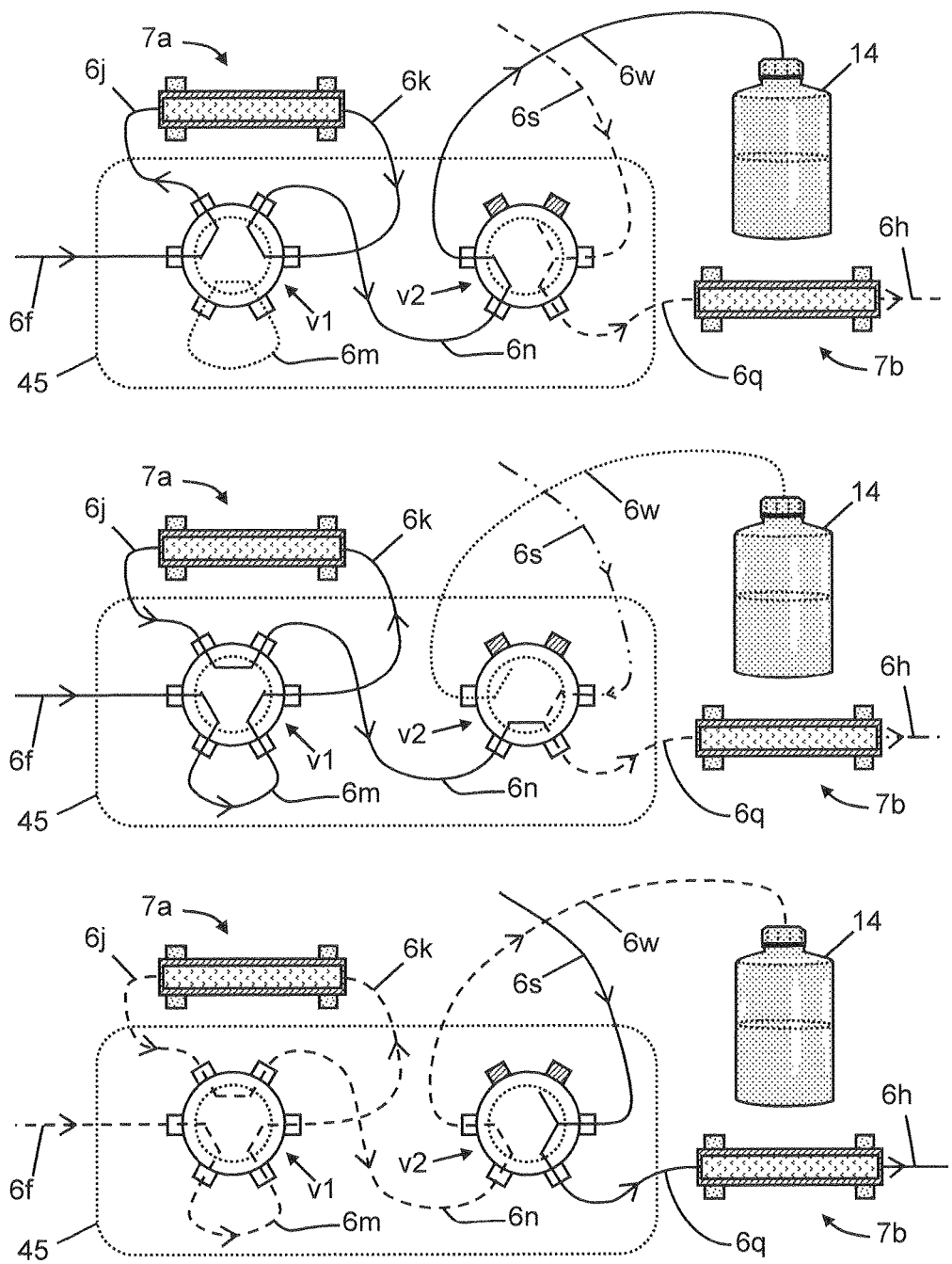
FIG. 5 is a schematic diagram showing an example of valve configurations and fluid flow paths steps that may be employed in a chromatography method employing the system of FIG. 4A.

FIG. 5 is a schematic diagram showing an example of valve configurations of the valve system 45 and fluid flow paths steps that may be employed in a chromatography method employing the system of FIG. 4A. The top, middle and bottom diagrams of FIG. 5 respectively illustrate: a sample loading step in which an analyte-bearing fluid is delivered to the first column 7a; a transfer step in which the at least partially purified analyte is mixed with a solvent in valve v2 and transferred to the second column 7b; and an eluting step, in which the analyte is eluted from the second column 7b and transferred to the detector (not shown in FIG. 5). In these diagrams, different flow paths are distinguished from one another by lines of different appearance (i.e., solid, dotted, dashed and dash-dot lines). Other modes of operation, utilizing alternative sets of valve configurations or sequences, are also possible.

Example 1—Fluid Monitoring and Verification

Figure 6:
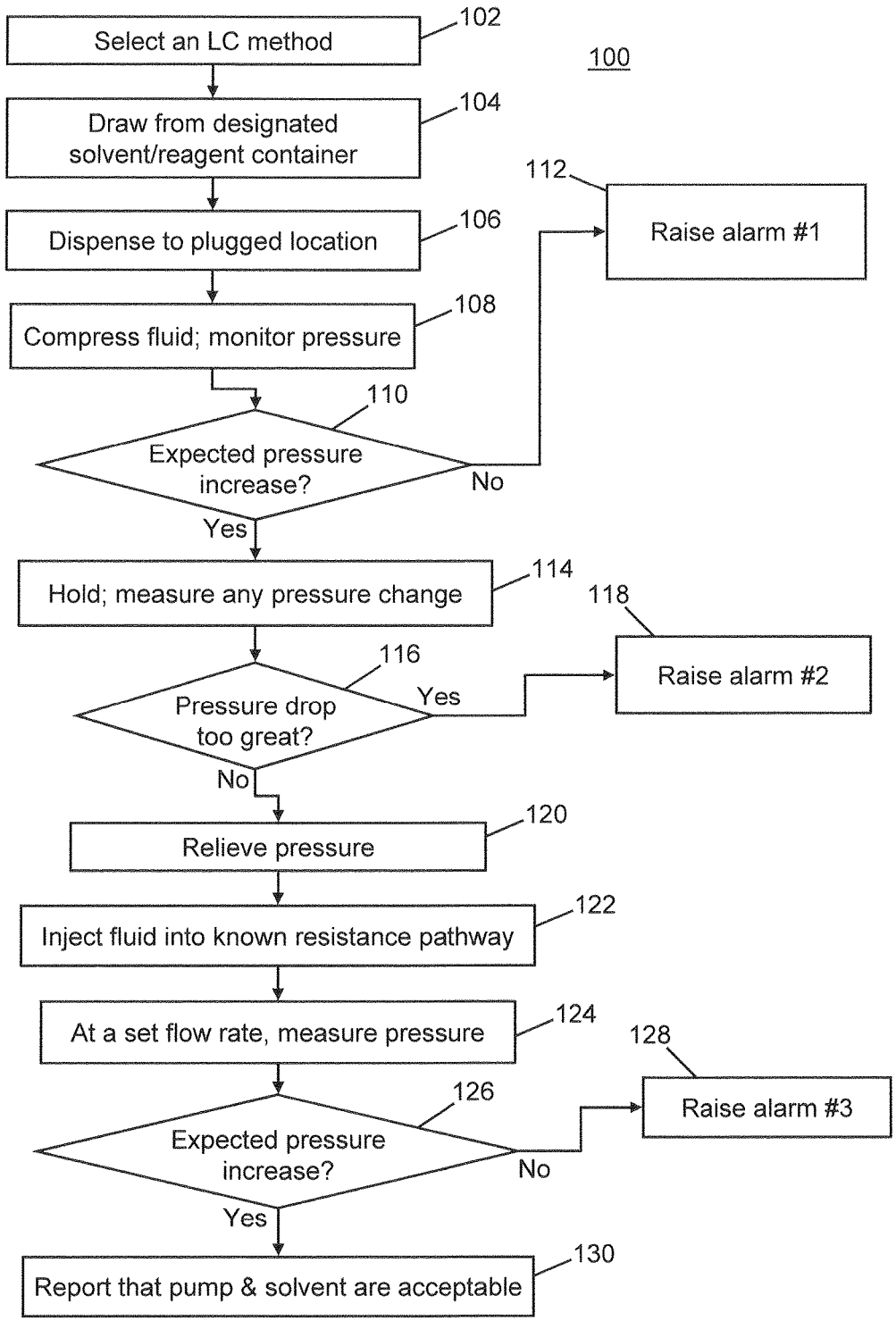
FIG. 6 is a flow diagram of a method for chromatography fluid monitoring and verification in accordance with the present teachings.

In accordance with the discussion presented above, FIG. 6 provides a flow diagram of a method 100 for chromatography fluid monitoring and verification in accordance with the present teachings. The method 100 may be executed by software or firmware of the computer or other electronic logic controller 32 in conjunction with signals transmitted along the electronic communication lines 34a, 34b and 34c. In the first step, Step 102 of the method 100, a user selects an LC method which includes solvents or reagents for which compressibility and viscosity information is available. In the next step, Step 104, a valve, such as the source valve 9r, is selected such that a pump (for instance, the syringe pump 11s) draws a fluid from a designated solvent or reagent bottle. In Step 106, the valve is configured so as to fluidically couple the pump cylinder, filled with the fluid drawn in step 104, to a plugged location, such as location p1 of the source valve 9r. In Step 108, the pump is operated so as to compress the fluid therein, while monitoring pump pressure, such as with sensor or gauge 16. Then, in the decision step, Step 110, if the observed rate of pressure increase (from Step 108) does not substantially match an expected value for an expected fluid, then the method execution is caused to branch to an execution termination or interruption step, Step 112, in which an alarm is raised that the solvent in the location from which the fluid was drawn may not match expectations. Upon observing the alarm, a user may perform any appropriate tests or checks to determine if the correct solvent or reagent is loaded in the position from which fluid was drawn. Depending upon the results of such tests or checks, the user may replace the solvent or reagent and re-start execution of the method 100 or, alternatively, may re-set the alarm (possibly, after solvent or reagent replacement) and continue execution of the method from the interrupted point.

If, during execution of step 108 of the method 100 (FIG. 6), the observed rate of pressure increase does indeed substantially match an expected value for an expected fluid, then step 110 branches execution to Step 114 in which, after obtaining a maximum useable pressure, the pump piston is held in place for a set amount of time while continuing to measuring any change or changes in pressure. In the subsequent decision step, Step 116, if an observed pressure drop is greater than an acceptable amount during the selected time, then execution is caused to branch to an execution termination or interruption step, Step 118, in which an alarm is raised that the pump in the given location may not be leak-free in accordance with expectations. Upon observing the alarm, a user may perform any appropriate tests or checks to determine if the pump is operating correctly. Depending upon the results of such tests or checks, the user may need to replace or repair the pump or other components and re-start execution of the method 100 or, alternatively, may re-set the alarm and continue execution of the method from the interrupted point.

The method 100 (FIG. 6) branches to Step 120 if, in Step 116, the observed pressure drop is determined to not exceed the acceptable amount during the selected time. In step 120, the pump may be operated, such as by moving a pump piston, so as to relieve the pressure in pump chamber. In the subsequent Step 122, the valve, such as source valve 9r, is operated so as to fluidically connect the pump with a fluid pathway having a known fluid resistance; in Step 124, the pump is operated so as to inject the fluid into such pathway at a set flow rate while the pump pressure is measured. In the subsequent decision step, Step 126, if the observed pressure increase (of Step 124) does not match an expected value, then execution is caused to branch to a termination or interruption step, Step 128, in which an alarm is raised that that the solvent in the location from which the fluid was drawn may not match expectations. Upon observing the alarm, a user may perform any appropriate tests or checks to determine if the correct solvent or reagent is loaded in the position from which fluid was drawn. Depending upon the results of such tests or checks, the user may replace the solvent or reagent and re-start execution of the method 100 or, alternatively, may re-set the alarm (possibly, after solvent or reagent replacement) and continue execution of the method from the interrupted point.

Execution of the method 100 proceeds to Step 130 if all pressure monitoring tests have yielded acceptable results. At this point, it may be reported to a user that the pump and solvent check passed with acceptable measurements. Subsequently, the valve may be configured so as to dispense the solvent or reagent into the system along fluid tubing line 6f (if the solvent is to be utilized) or to waste.

Alternative Hardware Configurations

Figure 7A:
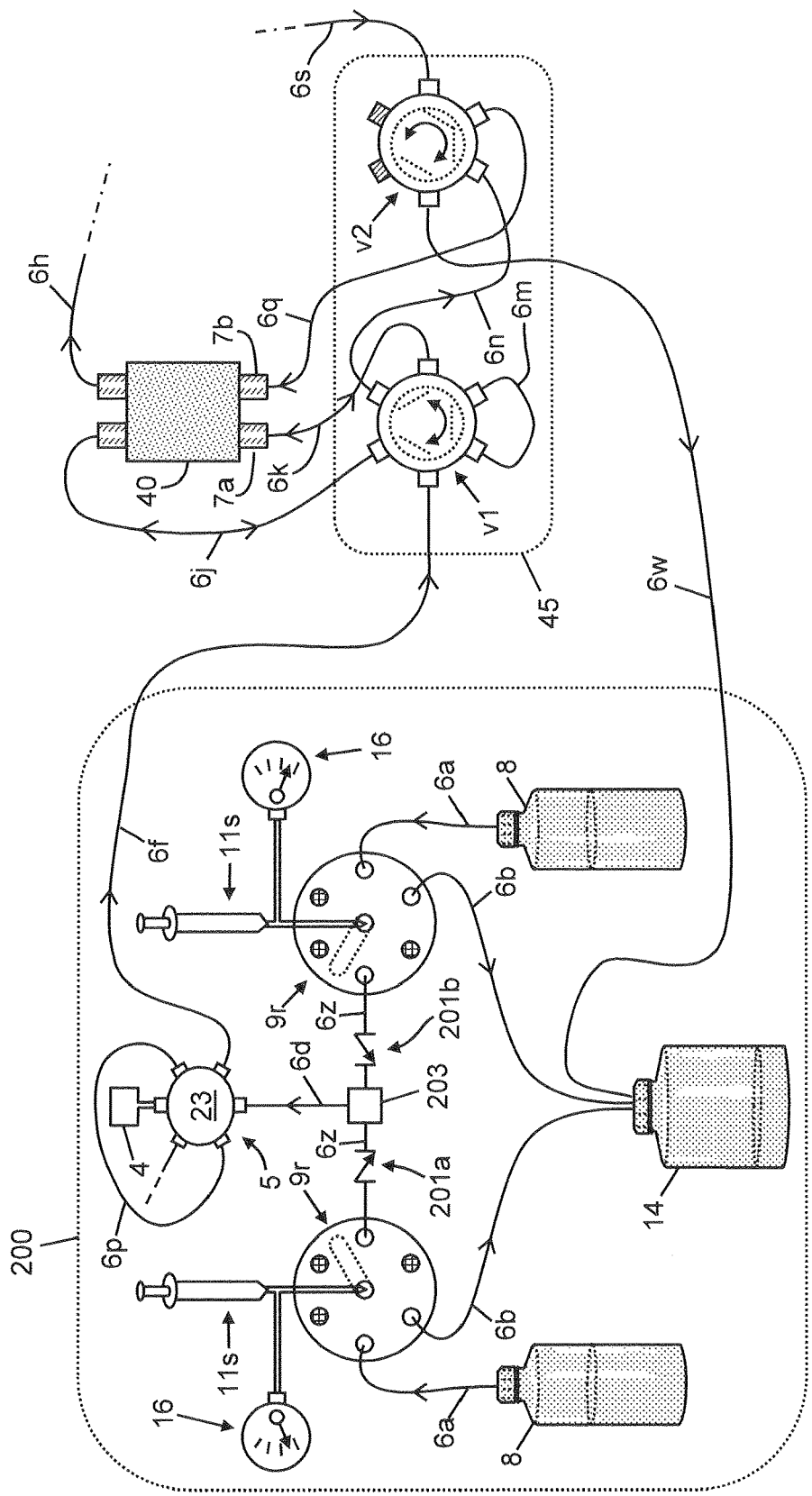
FIG. 7A is a schematic illustration of a sample source portion of an LCMS system according to some embodiments in accordance with the present teachings.

FIG. 7A is a schematic illustration of a sample source sub-system of an LCMS system according to some embodiments in accordance with the present teachings. The sub-system 200 shown in FIG. 7A may be employed as a loading system for loading analytes onto a chromatographic column. The sub-system 200 comprises a sample injector apparatus 5 and may comprise two or more syringe pumps 11s, respective associated pressure sensors or gauges 16, respective associated selection valves 9r, and respective solvent sources 8. Such components may be essentially similar to similarly-labeled components in FIG. 2. A dedicated waste container 14 may be included as part of the sample-source sub-system 200 or, alternatively, a single waste container or drain manifold may be employed for a chromatography system of which the sub-system 200 is a part.

Corresponding fluid tubing lines 6z leading from the selection valves are joined by a fluid coupling 203 which, depending on system application or configuration, may comprise a mixing tee or a selection valve. If more than two selection valves 9r are employed, then the coupling 203 may comprise a multiport valve or a cross coupling. The coupling 203 may be configured so as to selectively fluidically couple line 6d to either one one of the pumps or to fluidically couple line 6d to both pumps simultaneously. Alternatively, the coupling 203 may be configured as a three-way tee valve which could accomplish either selective coupling (to one pump or the other) or simultaneous coupling (to both pumps). One-way check valves 201a, 201b may be installed in one or more of the fluid tubing lines 6z so as to prevent fluid originating from a pump or valve in which the fluid is held at a high pressure from flowing back into a coupled second pump or valve in which a fluid is maintained at a lower pressure. If it is known that one pump will always be operating at a higher pressure than other pumps, then a check-valve may not be required on an output line associated with that pump.

The sample-source sub-system 200 shown in FIG. 7A may be used in place of the injector 5 shown in FIGS. 4A-4B. Accordingly, the sample-source sub-system 200 is illustrated, in FIG. 7A, as being fluidically coupled to the valve system 45 and associated two-column chromatographic cartridge 40 previously discussed in relation to FIG. 4B. Accordingly, an output fluid tubing line 6f delivers a mixture of sample plus solvents to a port of valve v1 of the valve system 45. As previously discussed, an output fluid tubing line 6h from the chromatographic cartridge 40 delivers separated chemical components to a mass spectrometer (not shown).

Figure 7B:
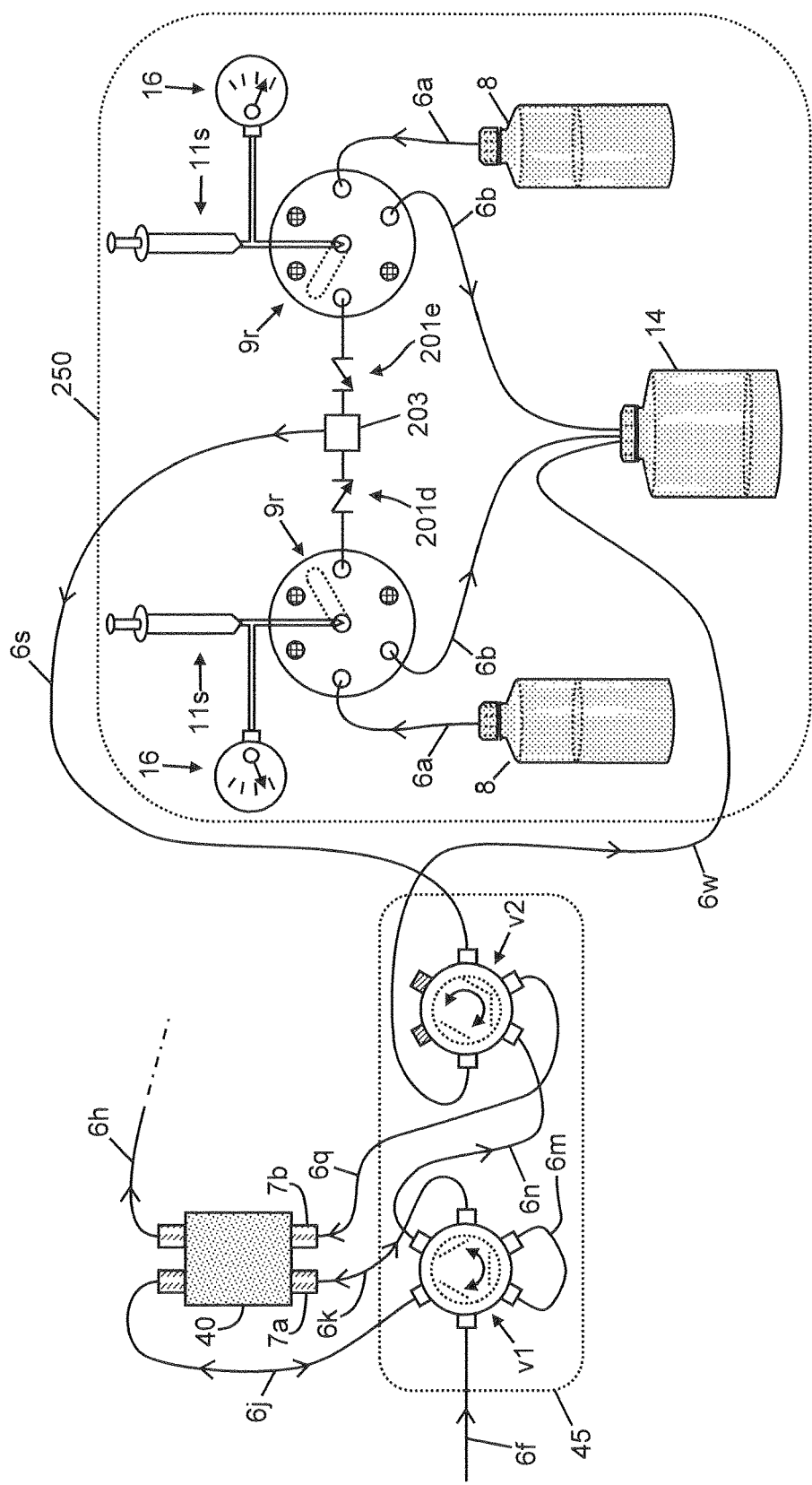
FIG. 7B is a schematic illustration a solvent source portion of still another LCMS system according to some embodiments in accordance with the present teachings.
Figure 7C:
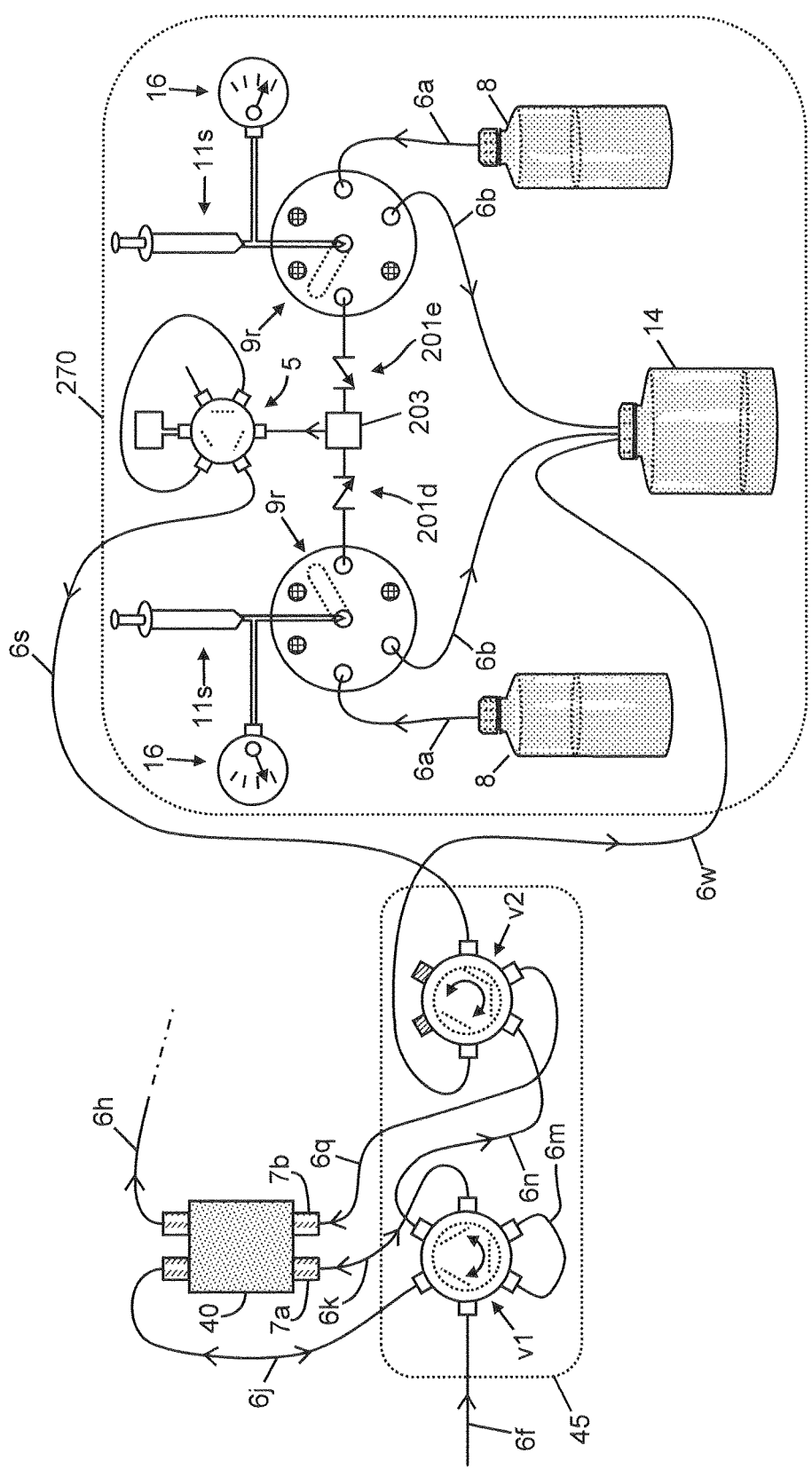
FIG. 7C is a schematic illustration a solvent source portion of yet another LCMS system according to some embodiments in accordance with the present teachings.

FIGS. 7B-7C are schematic illustrations of example solvent source sub-systems of an LCMS system according to some embodiments. The sub-system 250 illustrated in FIG. 7B may be employed as an eluting system for separating analytes previously loaded onto a chromatographic column. As shown, the solvent source sub-system 250 comprises many of the same components already described in relation to FIG. 7A. However, the sub-system 250 does not include an injector. Instead, solvents that are either mixed or selected at the fluid coupling 203 are directed, along fluid tubing line 6s, to a port of the valve v2 of the valve system 45. The sub-system 250 illustrated in FIG. 7C is similar to the sub-system 250 of FIG. 7C except that the sub-system 270 includes a second sample injector apparatus 5 installed along the fluid tubing line 6s. The provision of the second sample injector apparatus gives users the ability to inject sample on the second injector and thereby bypass the chromatographic column 7a within the cartridge 40. At those times when the second sample injector apparatus is not used, the valve portion of the second injector apparatus may be configured to route fluid received from the coupling 203 directly to valve v2. One-way check valves 201d, 201e may be installed in one or more of the fluid tubing lines leading from output ports of the pumps 9r so as to prevent fluid originating from a pump or valve in which the fluid is held at a high pressure from flowing back into a coupled second pump or valve in which a fluid is maintained at a lower pressure. If it is known that one pump will always be operating at a higher pressure than other pumps, then a check-valve may not be required on an output line associated with that pump.

Example 2—Observed Pressure Increase Versus Compressibility

Figure 8:
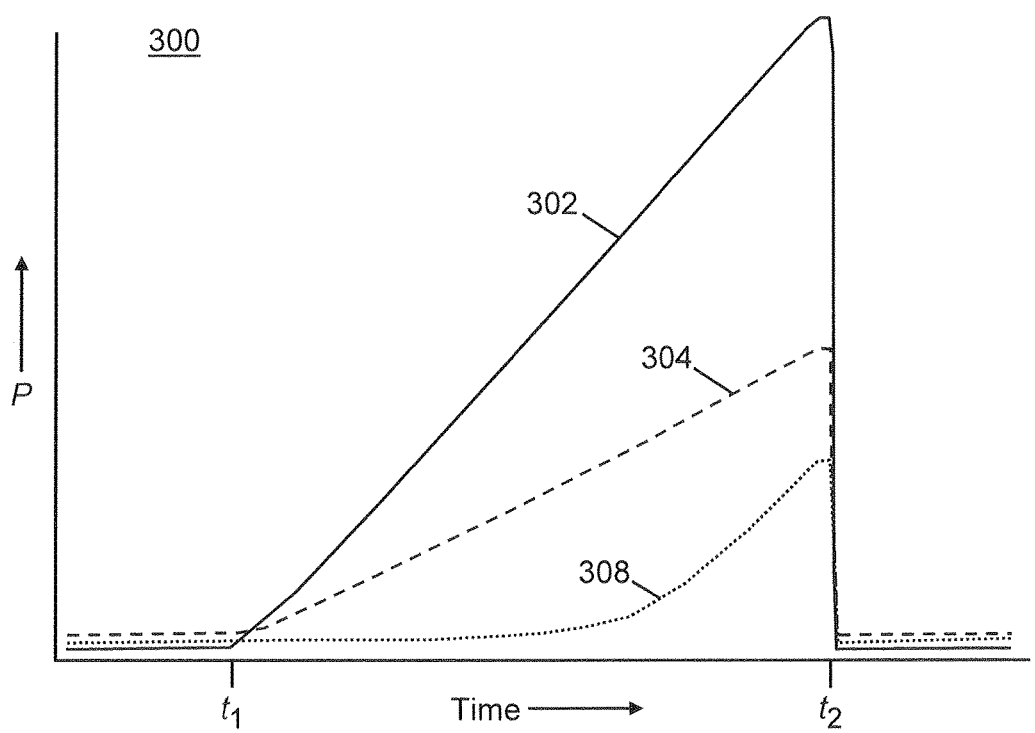
FIG. 8 is a graph showing a set of plots of observed pressure versus time for respective fluids as the fluids are compressed against a plugged port by movement of a syringe pump piston.

In order to determine, during routine chromatograph operation, if a measured pressure increase corresponds to a compressibility of an expected fluid (e.g., Step 110 of Method 100 outlined in FIG. 6), it is desirable to first generate pressure calibration data. FIG. 8 provides a graph 300 showing examples such data. The top two curves illustrated in FIG. 8—curve 302 and curve 304—are plots of pressure versus time for as observed for bubble-free water and methanol, respectively, as each fluid is compressed against a plugged port by movement of a syringe pump piston at a constant rate. In each case, compression is started at time $t_1$ and pressure is released at time $t_2$. As expected, the rate of pressure increase in such experiments is inversely related to the compressibility of each single-phase fluid within the syringe pump. However, if air or gas bubbles are present within a liquid, then the rising-pressure portion of the curve will be delayed, as is indicated by curve 308, which represents the same experiment performed on a two-phase fluid consisting of water and gas bubbles. If bubbles are present, the initial motion of the pump piston serves to collapse gas bubbles and, perhaps, cause dissolution of the gas into the liquid without substantial pressure increase. Such results can thus be utilized to monitor for and detect the presence of unwanted air or gas bubbles during routine operation.

Example 3—Monitoring Pump Pressure Integrity and Lifetime

Figure 9A:
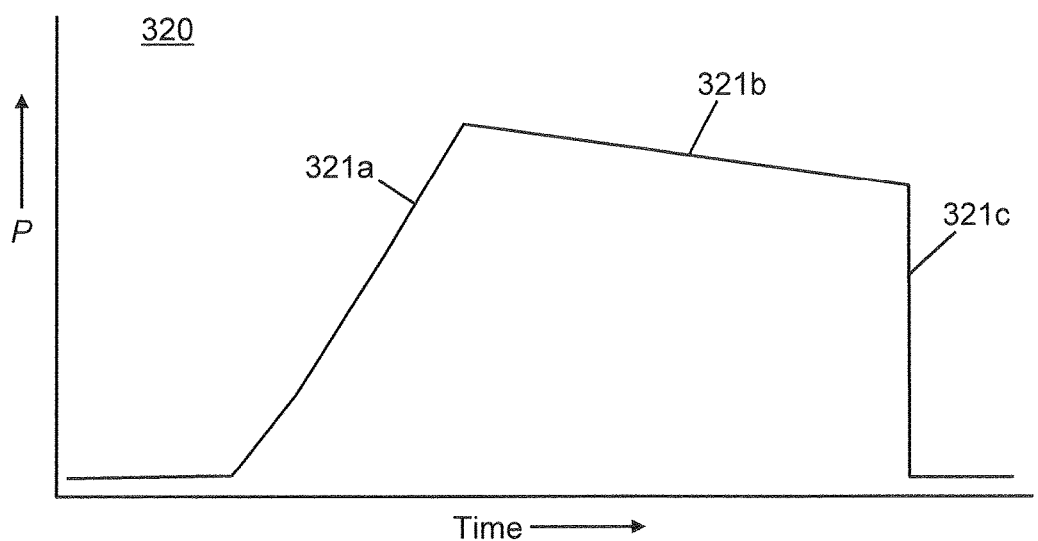
FIG. 9A is a schematic graph illustrating, in a general sense, a pressure profile within a syringe pump versus time in a situation in which the syringe pump is used to compress a fluid against a plugged port and subsequently maintain pressure.

Fluid compression experiments may also be employed to determine the pressure integrity of seals with a syringe pump as well as to develop predictive models that can alert a user that a pump is approaching failure. FIG. 9A schematically illustrates the general form of data obtained in such experiments. The curve in graph 320 represents the observed pump pressure during corresponding to two experimental segments. During the first such segment, a fluid is compressed by operation of a syringe pump while an output valve is directed to a plugged port. During this experimental segment, the observed pressure rises along curve segment 321a as a result of the finite compressibility of the fluid. During the second experimental segment the syringe pump is held motionless while the pressure drift—represented by curve segment 321b, is observed. During this time period, a slow decrease in internal pump pressure is observed—even with a new pump—because the pump and valve pressure seals are necessarily imperfect. Curve segment 321c represents release of pressure at the end of an experiment.

The slope of the curve segment 321b shown in FIG. 9A is diagnostic. If a syringe pump is repeatedly operated over many such compression and decompression cycles, the pressure-sealing ability of the pump will be observed to deteriorate over time. Stated differently, the leak rate, expressed as the rate of pressure change, will be observed to increase over time. If experiments such as those described in relation to FIG. 9A are periodically performed during the course of compression cycling, then the variation in leak rate versus pump lifetime may be modeled. If such experiments are then also periodically performed—either automatically or under the control of a user—during the course of routine pump operation, then the observed leak rate behavior may be compared with the model in order to predict remaining pump lifetime. Since the exact rate of pressure decay (i.e., the leak rate) may vary both with fluid type and with pump operating pressure, such leak rate experiments should be performed under standardized conditions. The pressure leak rate is observed to follow a curve such as the curve 352 shown in graph 350 of FIG. 9B.

Figure 9B:
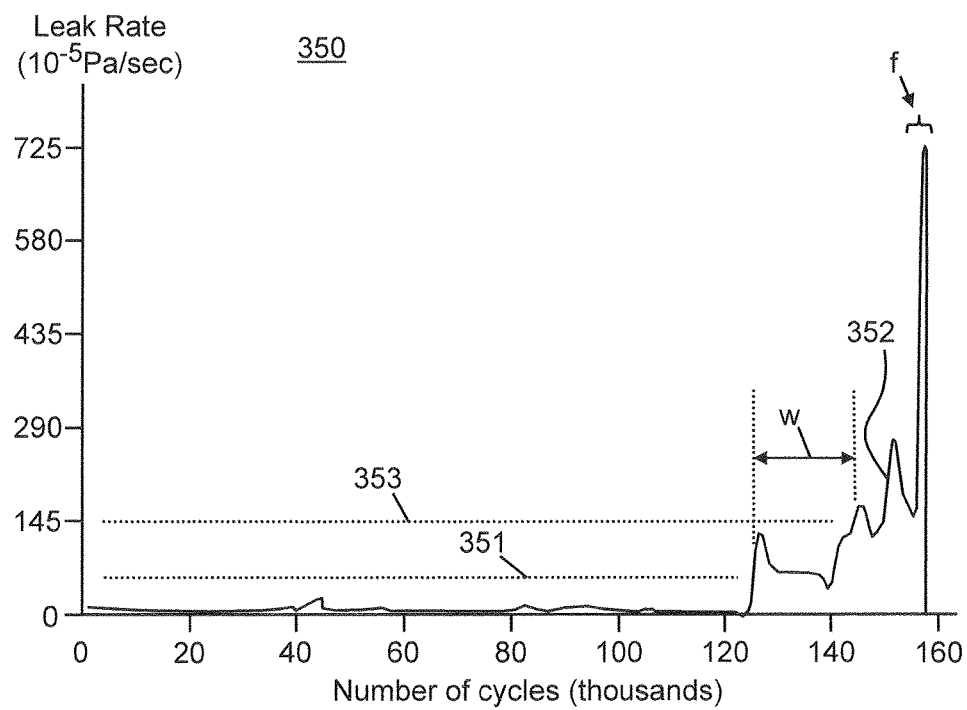
FIG. 9B is a graph showing experimental data of the observed pressure leak rate for a syringe pump (with valve) versus the number of cycles of actuation.

As indicated by the data plotted in FIG. 9B, the pressure leak rate of a syringe pump does not vary from its initial value, over an initial period encompassing most of the pump's usable lifetime, by more than a certain value. It is further observed that, at some time prior to total failure of the pump, the pressure-sealing ability of the pump will enter into a pre-failure condition, at the onset of which the leak rate rapidly increases to greater than twice the maximum leak rate observed during the initial period. The onset of the pre-failure condition is thus indicated by the leak rate initially exceeding the normal working threshold line 351 as indicated in FIG. 9B.

During routine operation, a chromatograph instrument can periodically or occasionally be operated so as to measure pressure decay according to a procedure such as that discussed in reference to FIG. 9A. The pressure decay measurements could be programmed to occur automatically at regular periods. With such data, it is possible to predict how many injection cycles may remain in a pump's useable lifetime according to model data (e.g., curve 352) previously determined. Once the pressure leak rate has been observed to exceed such a threshold, a warning may be issued to users that the pump is approaching the end of its useable lifetime and should soon be repaired or replaced. Such a warning or alert may be communicated during warning period w as indicated on FIG. 9B. Once the leak rate has exceeded a second threshold, indicated as warning threshold line 353 in FIG. 9B, the operation of the pump may no longer meet specifications and the pump will soon undergo complete failure at region f.

Figure 13:
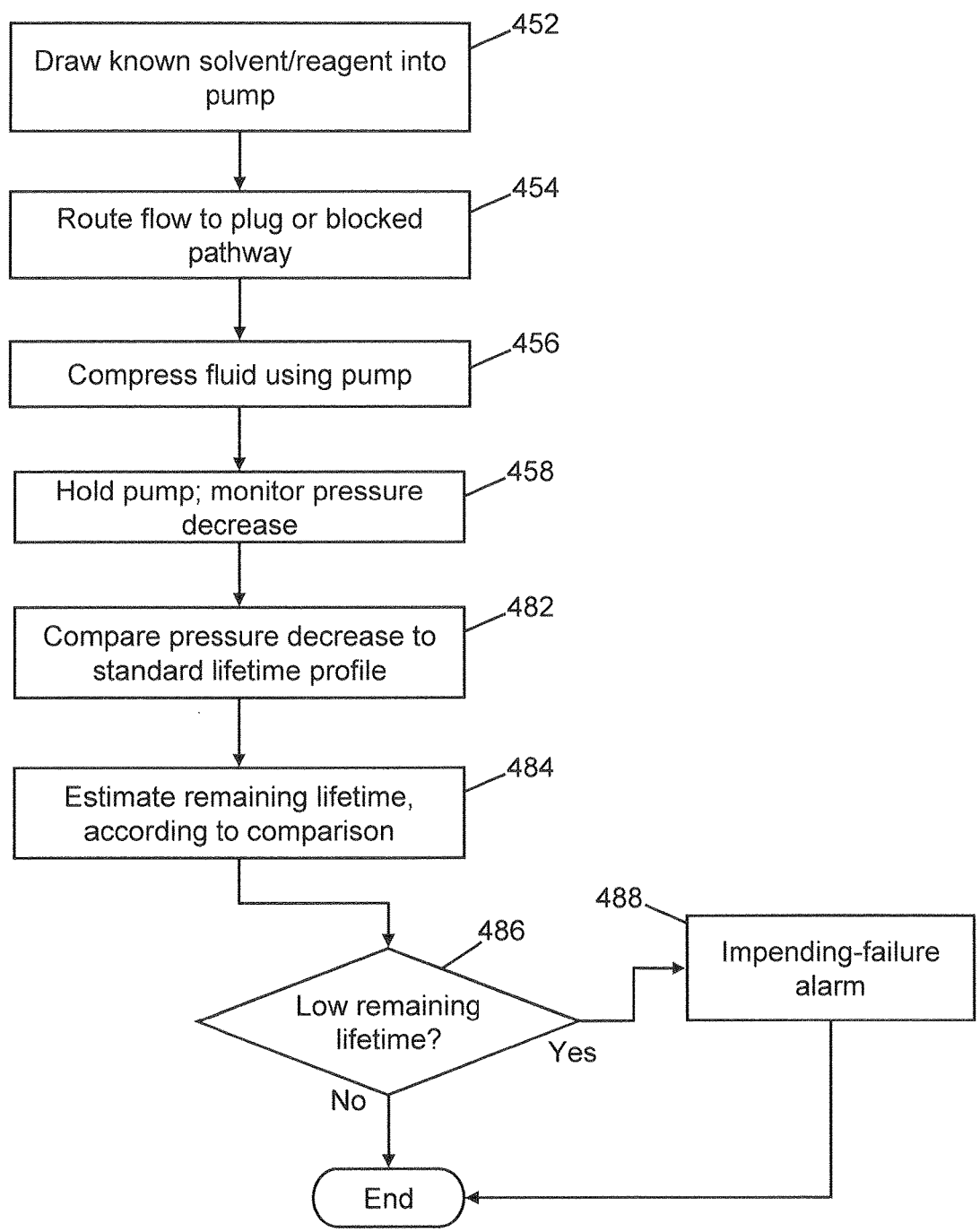
FIG. 13 is a flow diagram of a method for chromatography pump lifetime monitoring and testing in accordance with the present teachings.

FIG. 13 is a flow diagram of a method for chromatography pump lifetime monitoring and testing that illustrates the above concepts. In the first step, step 452, of the method 470 (FIG. 13), a known solvent or reagent is drawn into a syringe pump. In general, a syringe pump comprises a mechanically-driven piston which is fluidically sealed against and moves within a hollow cylinder so as to either draw fluid into a portion of the cylinder or to expel at least a portion of the fluid from the cylinder. If the output of the pump is blocked or if there is a blockage in a fluidic system to which the pump output is routed, then small movement of the piston will cause a compression of the fluid and a rapid pressure increase. Subsequent holding or maintaining of the syringe pump piston in a fixed position should correspond to no pressure change, if the pressure seals of the pump are perfect. In practice, a small rate of pressure decrease is normal and expected, since the seal is not perfect. With continued pump operation, however, wear in the seals and various mechanical components may lead to increasing rates or pressure loss when the syringe pump piston is maintained in a fixed position. Additionally, if leaks are present, the rate of pressure increase may be less than expected upon movement of the piston so as to compress the fluid, provided that the compressibility of the fluid in the pump cylinder is known.

Thus, in step 454 of the method 470 (FIG. 13), the fluid flow is routed to a blocked pathway. This step may be accomplished, for instance, by configuring a valve near the pump output—such as multiple-port rotary selection valve 9r illustrated in FIG. 3, so as to route the pump output to a plugged port, such as, for instance port p1 shown in FIG. 2. Accordingly, the valve is used so as to fluidically couple the pump to a plugged port. In the next step, Step 456, the pump piston is caused to move at a pre-determined rate in a direction which compresses the fluid between the piston and the plug. In Step 458, the compression is stopped and the pump piston is maintained or held in a fixed position while the pressure decrease, preferably of the fluid within the pump, is monitored. In the next step, Step 482, the rate of decrease is compared to a standard profile, such as profile 352 shown in FIG. 9B, that indicates the expected behavior of the pressure sealing capability of a pump throughout its lifetime. The profile 352 may be pre-determined, for instance, from prior experience with one or more pumps of the same type as the one being tested. In Step 484, an estimated remaining useful lifetime of the pump is determined, based on the comparison made in Step 482. If the estimated remaining lifetime (either in terms of time or operational cycles) is less than a certain threshold (Step 486), then a notification is provided or an alarm is raised (Step 488), as appropriate.

Example 4—Monitoring Pump Precision

In general, the mechanical movement of a piston of a syringe pump is controlled by a lead screw that is mechanically coupled to the piston. Accordingly, the precision of the pump, as determined by the precision of the fluid flow rate produced by action of the pump, depends upon the precision of the thread pitch of the lead screw and the thread pitch of mating threads in a mating threaded bore in which the lead screw moves. Likewise, deterioration in pump precision over time will be affected, at least in part, by wear of the lead screw threads and mating threads.

Figure 10:
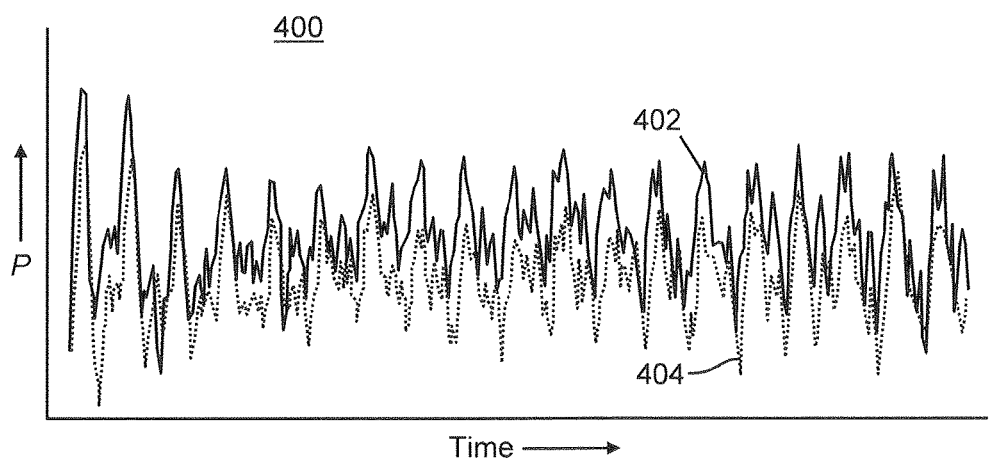
FIG. 10 is a graph showing two plots of observed pump chamber pressure versus time as a fluid is pumped from a syringe pump into a resistive tubing at a flow rate of 200 µl per minute.

If the pressure in a syringe pump chamber is continuously measured during operation of the pump so as to produce a constant nominal fluid flow rate through a flow resistive tubing (e.g., resistive tubing 6c in FIG. 2) or other component with constant fluid flow resistance, then the pressure is observed to follow a pattern such as indicated in graph 400 of FIG. 10. The two curves—curve 402 and curve 404—shown in FIG. 10 represent pump chamber pressure measured during two separate operations of a pump so as to pump water through a resistive tubing an a nominal constant flow rate of 200 µL/min. The pressure variation so measured is observed to vary cyclically with a periodicity that corresponds to the time for the lead screw to undergo a single rotation. In regards to the data plotted in FIG. 10, the average oscilatory pressure fluctuation is approximately five-percent of the total pressure, which is found to be normal for a new pump. Since the flow rate will approach a uniform average value over several cycles, this oscillatory pressure profile may be tolerable, depending upon the needs of users. However, some applications may require a tight tolerance on flow rates and measurements such as those shown in FIG. 10 may be employed to determine if a particular pump is within tolerance. Further, for any pump, the trend of ΔP may be monitored over the working lifetime of the pump, with any increase in this quantity being used to predict when wear on the pump mechanical parts will require pump maintenance or replacement.

Example 5—Detecting Leaks, Bubbles and Blockages in System

The pressure monitoring techniques described above in the context of detecting leaks of or air bubbles in syringe pumps may also be employed to detect problems relating to the fluidic components of an LSMS system. For instance, if there is a blockage in a fluid tubing line or other component, then the observed pressure should be higher than expected for a normally operating clean system. On the other hand, leaks may be detected by intentionally blocking or plugging one component of the LSMS system, pressurizing the portion of the fluidic system between the pump and the intentional blockage and, then, monitoring for any unusually high decreases in pressure.

In order to identify a particular portion of an LCMS fluidic system that is responsible for a problem, it is necessary to fluidically isolate specific portions of the system. One means of accomplishing such isolation is by replacing the two-column chromatographic cartridge 40 (FIG. 4B, FIGS. 7A-7C) with a special test cartridge that is employed only for system test purposes. Since the two-column chromatographic cartridge 40 is designed as a replaceable module, the replacement cartridge should be designed so as to be easily swapped for the column-containing cartridge and to allow for easy re-insertion of the column-containing cartridge.

Figure 11A:
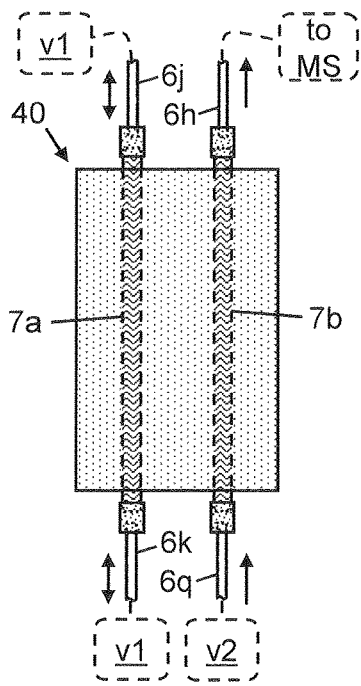
FIGS. 11A-11D are illustrations, respectively, of a normal chromatographic cartridge having two columns, a cartridge for system test purposes having two unobstructed tubes, a second cartridge for system test purposes having one unobstructed tube and one plugged line, and a third cartridge for system test purposes having two plugged lines.
Figure 11B:
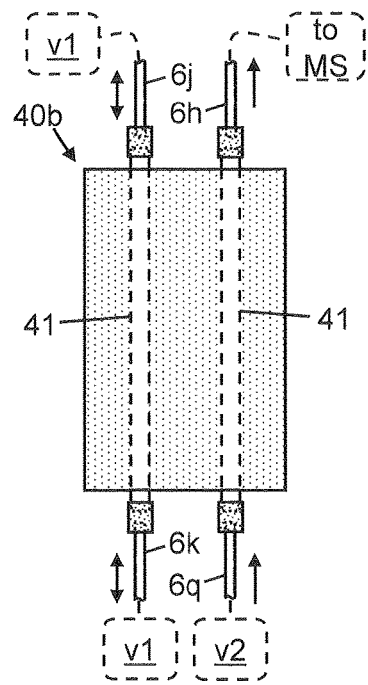
Figure 11C:
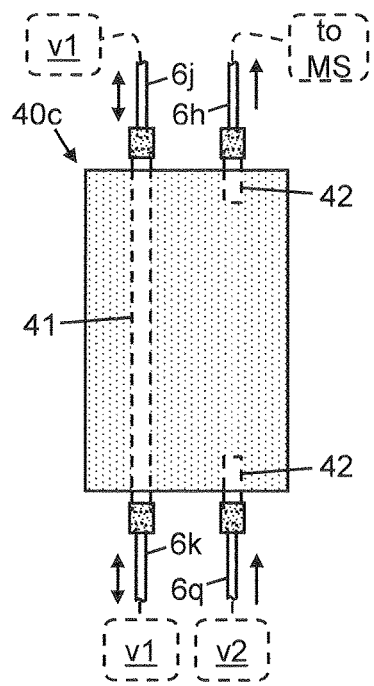
Figure 11D:
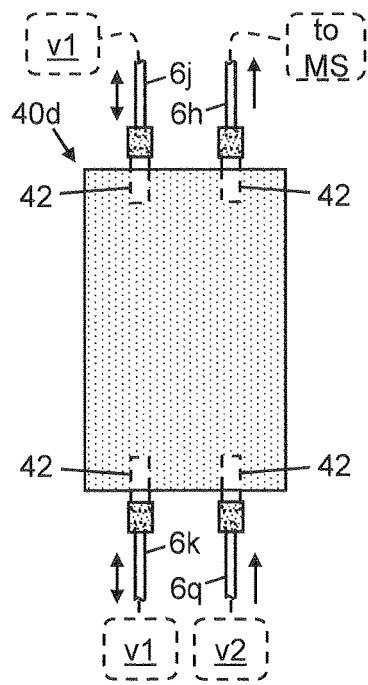

FIG. 11A illustrates the two-column chromatographic cartridge 40 having a first column 7a and a second column 7b. FIG. 11B shows a first test-related cartridge 40b that is designed to be swappable with the cartridge 40. In the test-related cartridge 40b, the columns 7a, 7b are replaced by two simple tubes 41 which are designed to permit unrestricted flow through the cartridge 40b. By using the test-related cartridge 40b, fluid can be routed through an entire LCMS system so as to detect any blockages. FIG. 11C illustrates a second test-related cartridge 40c, which is related to the two-column cartridge 40 by replacement of first column 7a with a simple tube 41 that permits unrestricted flow between fluid tubing lines 6j and 6k and replacement of the column 7b by one or more plugs 42 so as to prevent flow between fluid tubing lines 6q and 6h. This configuration permits one portion of the fluidic system to be isolated for detection of leaks or bubbles within that portion while permitting free flow through the other section. FIG. 11D illustrates a third test-related cartridge 40d, which is related to the two-column cartridge 40 by replacement of both chromatographic columns 7a, 7b with plugs or other blockages 42.

The test-related cartridges illustrated in FIG. 11 are just a few examples. One can also easily envision an alternative cartridge configuration, for instance, in which unrestricted fluid flow is permitted between fluid tubing lines 6q and 6h while the coupling between fluid tubing lines 6j and 6k is plugged or otherwise blocked. One can also easily envision other cartridge configurations which include a chromatographic column in one position with the other position occupied by a tube 41 or by one or more plugs 42.

Figure 12A:
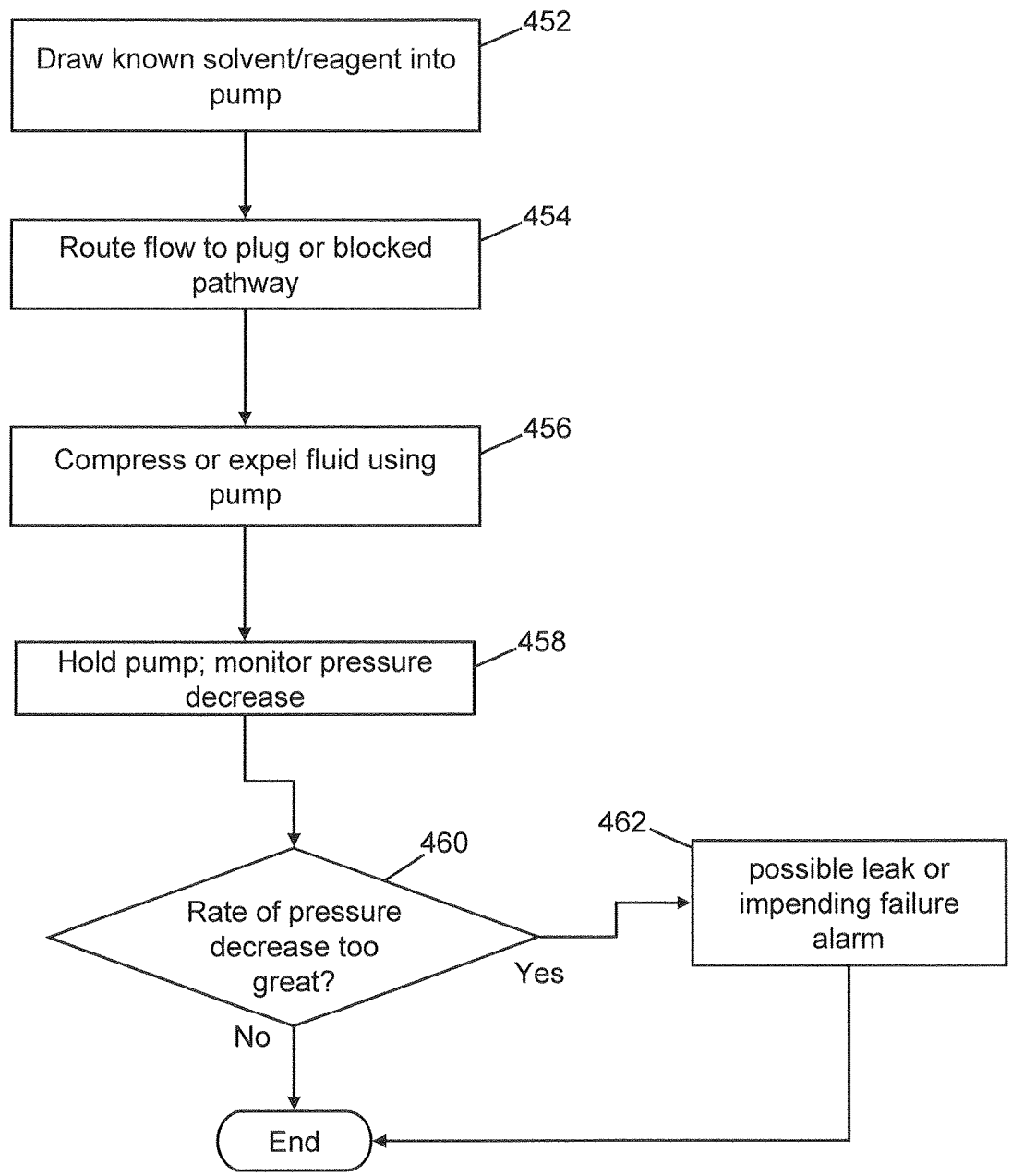
FIG. 12A is a flow diagram of a method for chromatographic system leak monitoring and detection in accordance with the present teachings.

FIG. 12A is a flow diagram of a general method for monitoring or detection of leaks in a liquid chromatography system, in accordance with the discussion in Example 5. The method 450a illustrated in FIG. 12A may be applied to leak detection and monitoring of pumps but, more generally, may also be applied to leak detection and monitoring throughout an entire fluidic system. Steps 452-458 of the method 450a are the same steps shown in and already discussed in regard to FIG. 13. However, it is here noted that the "blocked pathway" referred to in Step 454 need not be limited to the vicinity of a pump but may be placed anywhere in the fluidic system. Thus, the blocked pathway may be associated with any component anywhere in the system, such as a valve or an insertable and removable plug, or an insertable or removable cartridge, etc., which may be configured to inhibit flow past the blockage. Multiple such intentional blockages may be employed, in sequence, at different points within the fluidic system so as to isolate and identify any leaks. In Step 456 of the method 450a, the compression of the fluid may occur not only in a pump but also within a portion of the fluidic system. Thus, some fluid may be necessarily expelled from the pump into the portion of the fluidic system. The pressure monitoring in Step 458 should preferably be performed with a pressure sensor in close proximity to the fluidic system portion of interest. If, in the decision step (Step 460) the pressure decrease determined in Step 458 exceeds a certain pre-determined threshold, then an alarm is raised or a notification made in Step 462.

Figure 12B:
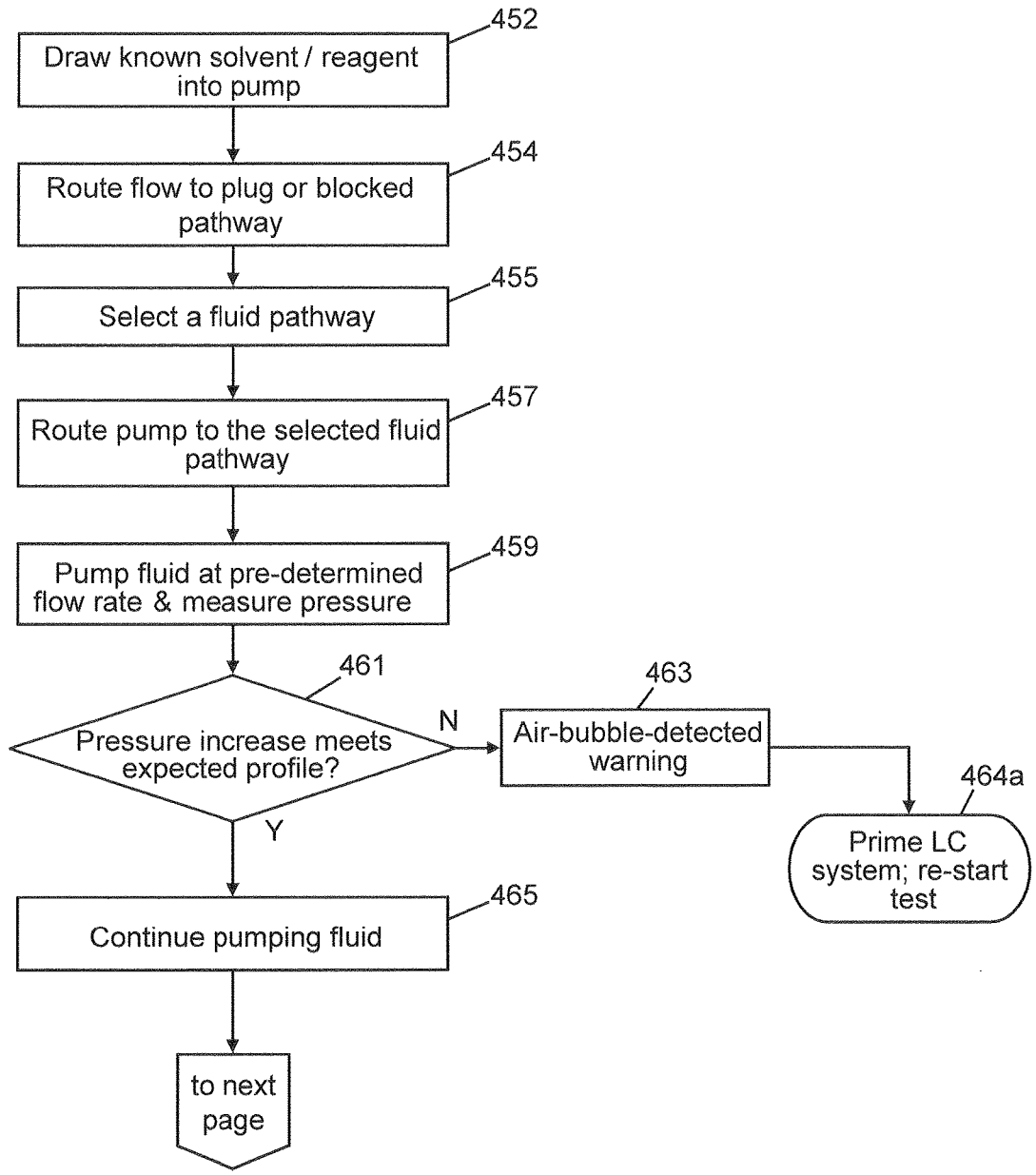
FIG. 12B is a flow diagram of a second method for chromatographic system leak monitoring and detection in accordance with the present teachings.
Figure 12B:
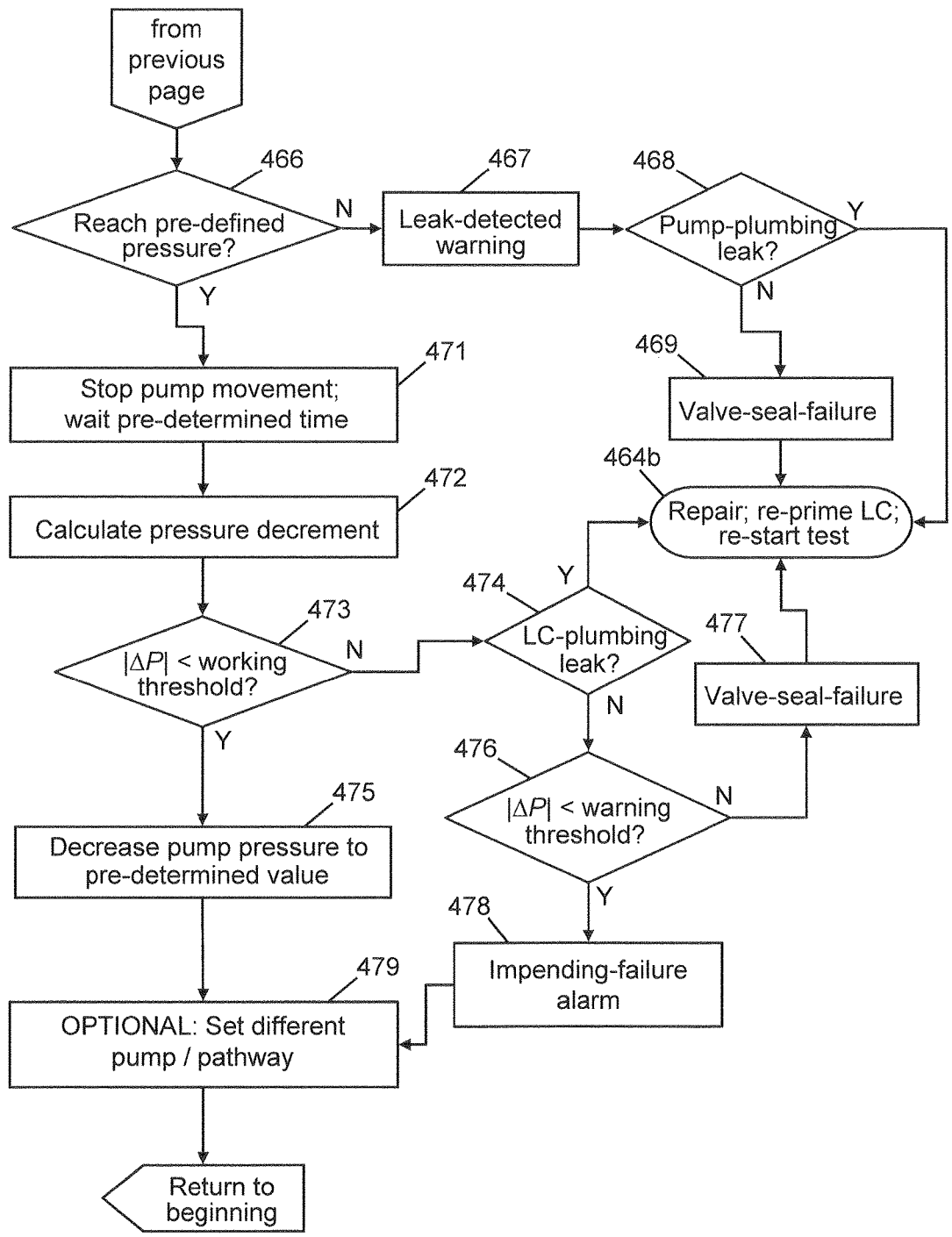

FIG. 12B is a flow diagram of a second method for monitoring or detection of leaks in a liquid chromatography system in accordance with the present teachings. The method 450b illustrated in FIG. 12B is somewhat similar to the method 450a (FIG. 12A) but includes additional provisions for monitoring multiple fluid pathways within an LC system, for detecting bubbles, for warning of impending pump failure and for at least partially isolating the locations of leaks. The first steps—Step 452 of drawing in a known solvent or other fluid and Step 454 of routing flow to an intentionally blocked pathway—of the method 450b are the same as the corresponding steps in the method 450a. Then, in Step 455 and Step 457, respectively, a fluid pathway is selected and the system is configured—such as by configuring one or more valves—so as to route the pump output to the selected fluid pathway. In Step 459, the fluid is pumped into the fluid pathway at a predetermined flow rate while the pressure is simultaneously measured.

In the decision step 461 of the method 450b, if the pressure increase meets the expected pressure increase profile—that is, if the pressure increase is not less than that expected from a pre-determined profile, within tolerance—then pumping continues at Step 465. Otherwise (if the pressure increase is less than that expected), then one or more air or gas bubbles or pockets are interpreted to be present in the fluid pathway and a warning or notification of this condition is provided at Step 463. At this point, the method terminates (Step 464a) so that a user or technician may prime the LC system, after which the method may be started again from the beginning.

After a period of pumping fluid into the selected pathway (Step 465), a determination is made (in Step 466) as to whether the selected fluid pathway is capable of achieving some pre-defined pressure within a prescribed time or within a prescribed movement of the pump piston. If not, then a leak in either the pump plumbing system or the valve seal is interpreted to be present and a warning or notification to this effect is made in Step 467. If the presumed leak is determined not to be in ancillary pump plumbing components (Step 468) than a notification or warning of a valve seal failure may be made in Step 469. At this point, the method terminates (Step 464b) so that a user or technician may make any necessary repairs and prime the LC system. After making such repairs and priming, the method may be started again from the beginning.

If it is determined, in Step 466, that the selected fluid pathway is capable of achieving the pre-defined pressure within the prescribed time or piston movement, then pump movement is stopped (Step 471) and pressure decrease is monitored for a certain pre-determined length of time. If the change in pressure within the pre-determined time is denoted as the negative quantity $\Delta P$, then the pressure decrement—that is, the amount by which the pressure decreases—is given as $|\Delta P|$. This pressure decrement is determined in Step 472 and, a subsequent determination is made in Step 473 as to whether this pressure decrement is less than a pre-defined normal working threshold. The normal working threshold is defined such that, if the pressure decrement is less than this threshold, then the fluidic components within the selected pathway are presumed to be operating normally.

If the pressure decrement as defined above is greater than or equal to the working threshold value, then a leak is presumed to be present either in fluidic plumbing components of the pathway or in a valve seal of a valve within the pathway. If, in Step 474, it is determined—possibly by visual inspection—that there are leaks in the LC plumbing system, then the method terminates at Step 464*b*. Otherwise, if there are no leaks in the plumbing system, then a determination is made (Step 476) as to whether the pressure decrement is less than a warning threshold. This determination may be considered to be a test of the severity of any valve-seal leak. A pressure decrement above the normal working threshold but below the warning threshold (the warning threshold value being always greater than the normal working threshold value) is interpreted to mean that a valve seal, while presently still useable, is in danger of failing in the near future. In such a situation, a warning to this effect is provided in Step 478, after which a different fluid pathway may be set in Step 479. If the pressure decrement is determined, in Step 476, to be greater than or equal to the warning threshold, then a valve-seal failure has occurred and a notification to this effect is provided in Step 477 and the method terminates at Step 464*b*.

Step 475 of the method 450*b* (FIG. 12B) is executed if the pressure decrement has been determined (Step 474) to be less than the normal working threshold. In Step 475, the pump pressure is decreased to some pre-determined value, after which a different fluid pathway may be selected in Step 479 so that the method 450*b* may be employed, from the beginning, to test the different pathway.

Figure 14:
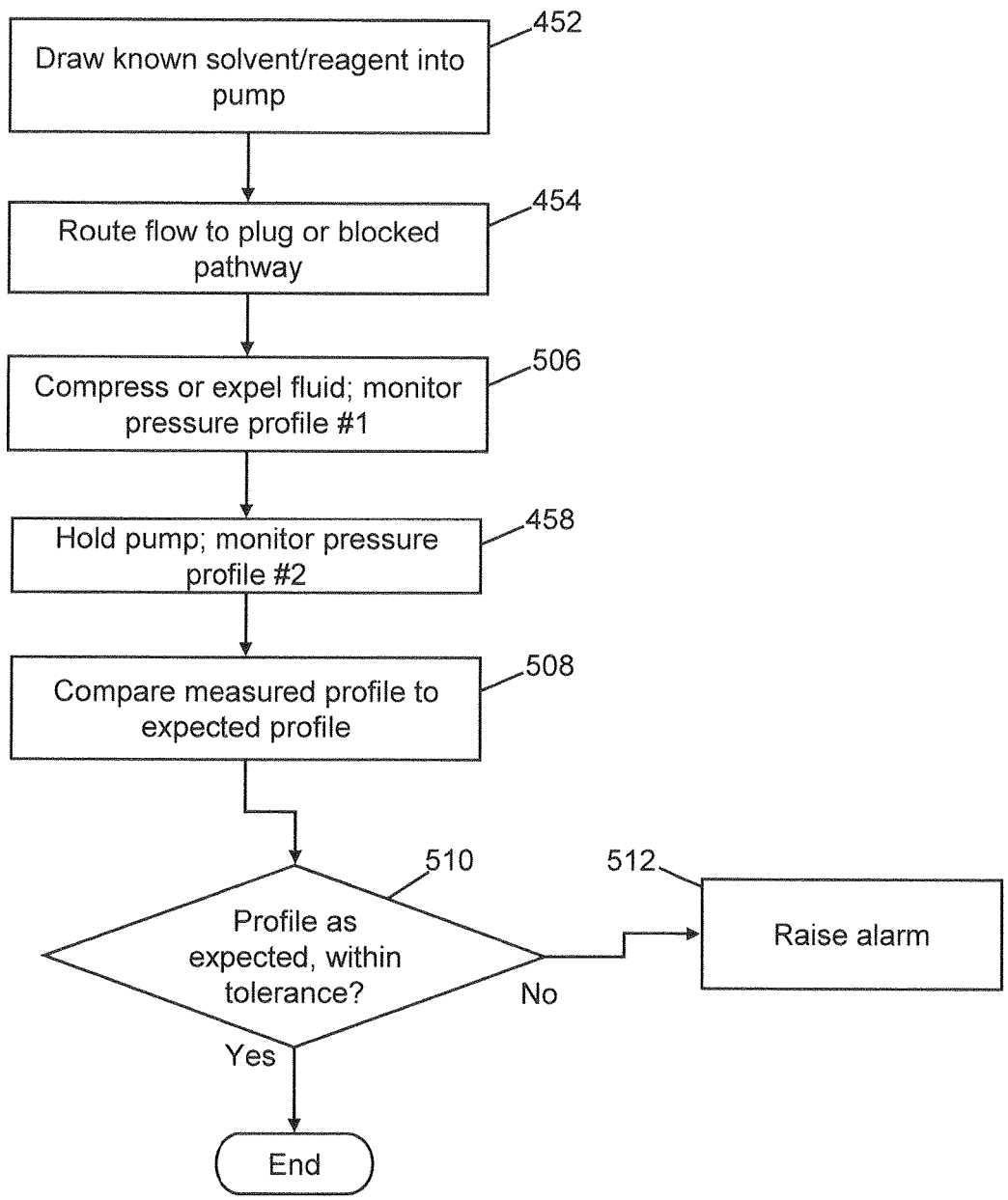
FIG. 14 is a flow diagram of a method for monitoring a liquid chromatography system in accordance with the present teachings.

Method 500 illustrated in flowchart form in FIG. 14 is a further generalization of the previously discussed methods 480 (FIG. 13) and 450*a* (FIG. 12A). Thus, although Steps 452, 454 and 458 of the method 500 are as previously described, the method includes a new step, Step 506, that replaces the previously described Step 456. In Step 506, pressure is monitored during the compression step so as to produce a first segment (segment #1) of a pressure profile. This is combined with the decreasing pressure profile (segment #2) measured in Step 458 to yield a multiple-segment pressure profile. The measured multi-segment profile is compared, in Step 508, to a multi-segment expected profile, such as the schematic profile illustrated in FIG. 9A. If the measured multi-segment profile is not the same as the expected profile, within a tolerance (Step 510), then an alarm is raised (Step 512). For example, by comparing pressure changes during the compression step (i.e., segment #1) to expected values, air or gas bubbles within the general fluidic system may be detected. Such bubbles will be observed as an initial delay in pressure increase, relative to expected profiles. In principle, multiple intentional blockages may be employed, in sequence, at different points within the fluidic system so as to isolate and identify the location of any included air or gas bubbles.

Figure 15:
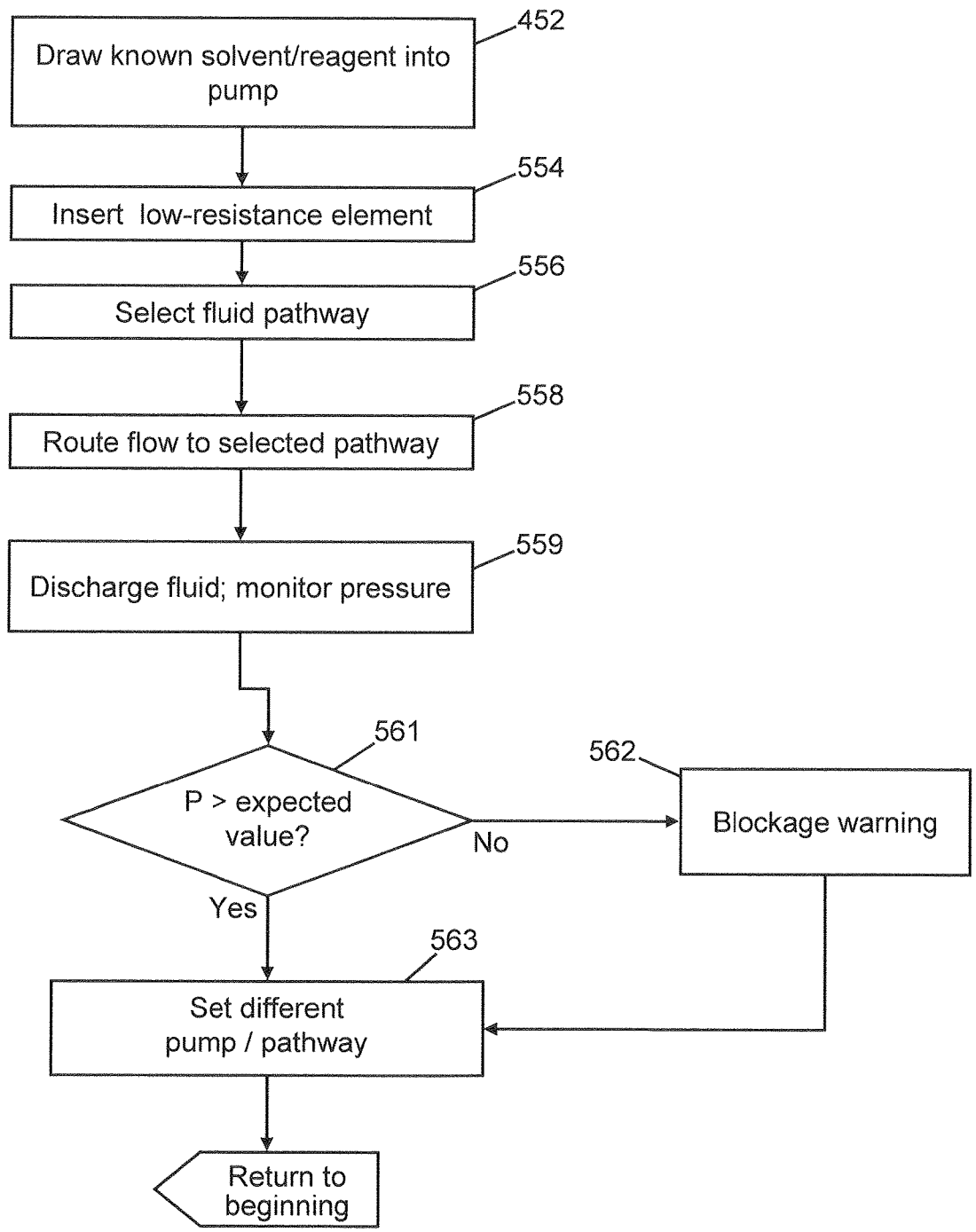
FIG. 15 is a flow diagram of another method for monitoring a liquid chromatography system in accordance with the present teachings.

FIG. 15 illustrates another method for monitoring a liquid chromatography system, in accordance with the present teachings. The first step, Step 452, of the method 550 (FIG. 15) is as previously described and comprises drawing a known solvent or reagent into a pump. In the next step, Step 554, the flow is routed through either an un-blocked fluidic pathway or through a fluidic pathway comprising a known low resistance to fluid flow. In this context, an "un-blocked" pathway is a pathway within which an ordinarily-employed flow-resistive component has been temporarily replaced, for testing or monitoring purposes, by a simple tubing or otherwise open conduit, thereby enabling free flow through the tubing or conduit and downstream portions of the fluidic pathway. For example, the replacement tubing or conduit may replace one or more chromatographic columns so as to permit free flow of fluid through and past the nominal location of the column. The tubing segments 41 in the special test-related cartridges 40*b* and 40*c* (FIGS. 11B-11C) are examples of such temporarily installed open pieces of tubing. The fluid routing may be accomplished by means of configuring a valve, as has been previously described herein.

In Step 556 of the method 550 (FIG. 15), a particular fluid pathway is selected. Then in Step 558, various valves may be configured to route the the solvent, reagent or other fluid to the selected pathway. In Step 559, the fluid is at least partially discharged from the pump and thereby caused to flow using a pre-defined or a real-time-calculated flow rate through the low resistance element or un-blocked pathway of the fluidic system (as provided in Step 554), during which fluid pressure is monitored in real-time. The accumulated fluid pressure data comprises a measured pressure profile, which is compared to an expected pressure profile in Step 561. Alternatively, one or more individual pressure data points (at certain times) may be employed, instead of a full profile. If the measured profile (or value of a measured pressure data point) is greater than, within a tolerance, the expected or specified profile or value (Step 561), then an alarm is raised or other notification provided (Step 562) that flow through at least a portion of the system is blocked. The entire procedure may be repeated with a different selected pathway (Step 563). The expected profile may depend upon the particular fluid properties of the known solvent. The entire pressure profile or any portion of the pressure profile may be employed for making the comparison in the decision step 561.

Example 6—Real-Time Pressure Compensation

Using the LCMS system configurations illustrated in FIGS. 7A-7C, it is possible for pressure imbalances to develop between different sections of an overall system. Real-time pressure monitoring and compensation may be employed to re-balance the pressures. At least two different scenarios, described below, are possible.

In a first pressure-compensation scenario, two initially mutually isolated portions of a fluidic system are initially pressurized at different respective pressures. The different pressures could arise as simply as a consequence of one pump—associated with the first portion—being inactive at the time that a second pump—associated with the second portion—is operating. The different pressures could also variously arise as a consequence of different fluid properties, different required flow rates or different inherent flow resistances in the two portions. In this scenario, the two portions are subsequently fluidically coupled for the purpose of blending or mixing of the fluids. The fluidic coupling between the two system portions may be brought about by re-configuring a valve, for instance. When the two portions are fluidically interconnected, conventional systems will experience a sudden pressure drop in the portion that was initially at the higher pressure.

Figure 16A:
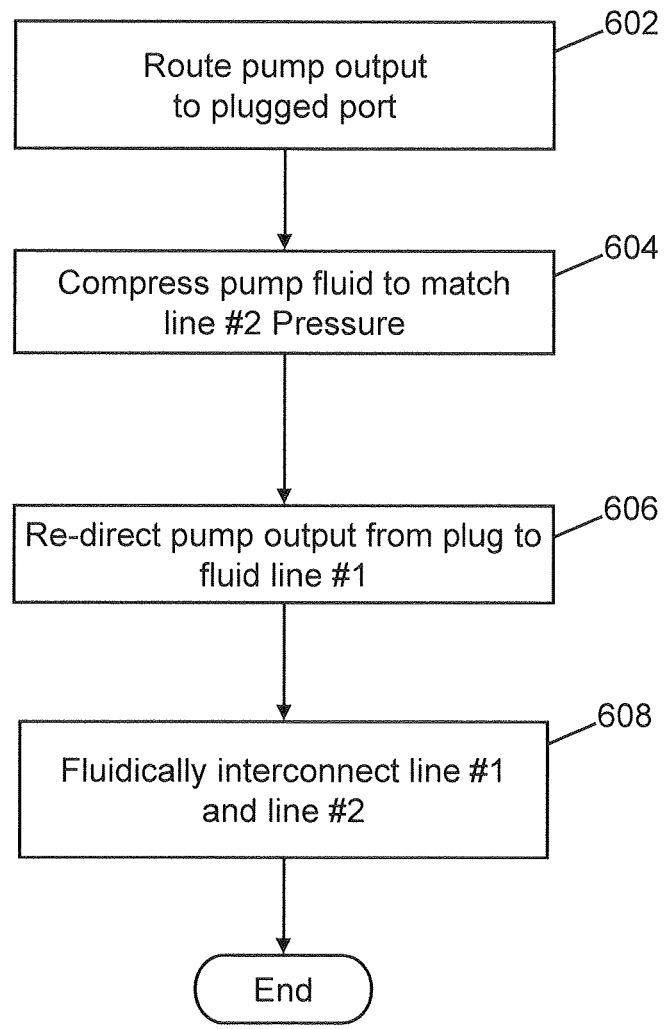
FIG. 16A is a flow diagram of a method for balancing pressure in different portions of a liquid chromatography fluidic system in accordance with the present teachings.

To prevent an unwanted pressure drop from occurring in the scenario described above, the following steps, according to the instant teachings and outlined in FIG. 16A, may be employed: (a) directing the output of the pump associated with the lower-pressure portion (fluid line #1, for identification purposes) to a plugged output (Step 602 of method 600 shown in FIG. 16A); (b) compressing the fluid within the pump while monitoring the pressure of the higher pressure portion (fluid line #2), thereby matching the pressure in the pump to the pressure in fluid line #2 (Step 604); directing the output of the pump to the fluid line #1 so at to increase the pressure within fluid line #1 (Step 606); and fluidically interconnecting fluid line #1 and fluid line #2 (Step 608). Step 602 of directing the pump output to a plugged output may be performed, for example, by rotating an appropriate rotary valve 9r (FIGS. 2, 7) to one of the plug positions shown by cross-hatching, such as plug position p1 illustrated in FIG. 2.

Figure 16B:
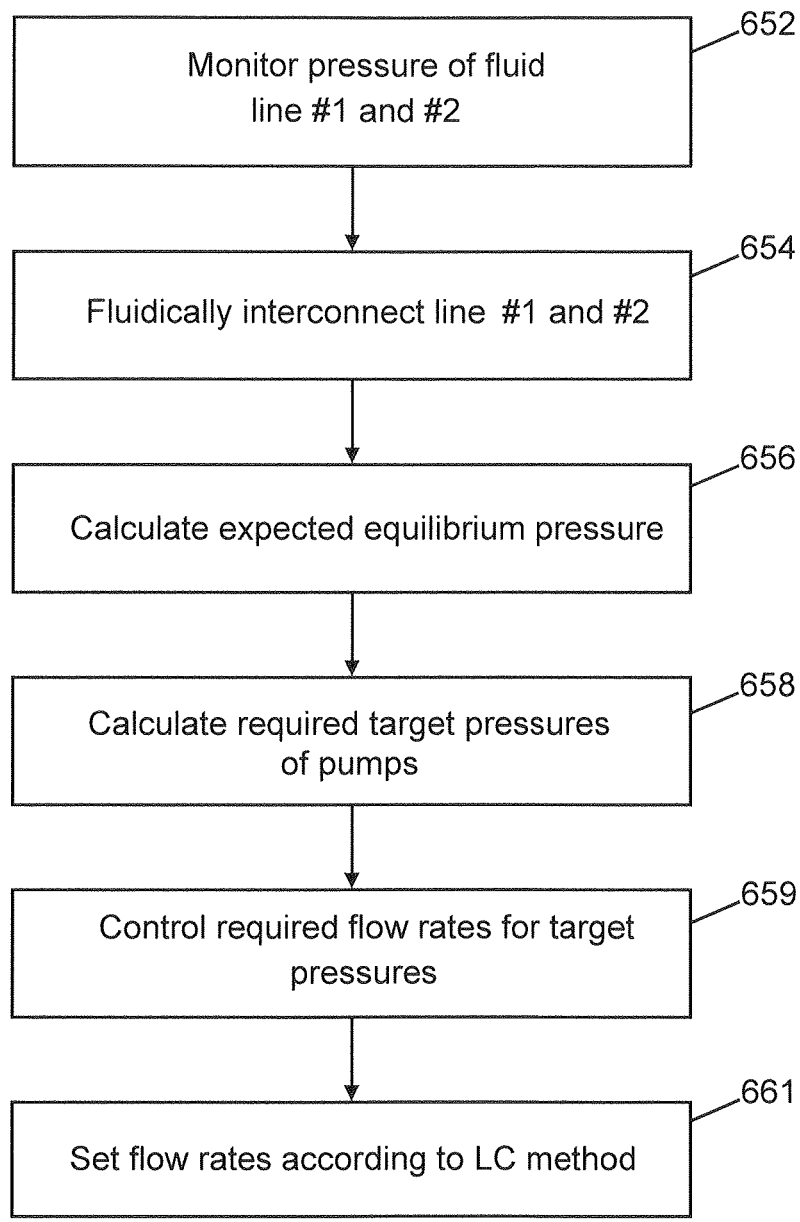
FIG. 16B is a flow diagram of a method for compensating pressure differences in different portions of a liquid chromatography fluidic system in accordance with the present teachings.

FIG. 16B is a flow diagram of a method for compensating pressure differences in two fluid lines which are to be employed for fluid flow at flow rates specified by a particular liquid chromatography method. In Step 652, the pressures of fluid line #1 and fluid line #2 are monitored or measured. Then, in Step 654, the two fluid lines are interconnected, such as by configuring one or more interconnection valves. In Step 656, an expected final equilibrium pressure (or pressures) is (are) calculated based on the pressures before interconnection and as a function of flow rate. In Step 658, the target pressures of the pumps are set at the expected equilibrium pressure or respective pressures by, for example, compressing fluid within the pumps against plugged output ports. Then, in Step 659, the flow rates are controlled so as to reach the target pressure using a control algorithm such as the well-known proportional-integral-derivative (PID) control algorithm. Finally, in Step 661, the flow rates are rates are re-set to the specific flow rates specified in a particular liquid chromatographic method that is to be performed by the system.

In another pressure-compensation scenario, pressure compensation may be employed so as to balance pressure differences between a loading pump sub-system, perhaps configured similar to sub-system 200 shown in FIG. 7A and an eluting pump sub-system, possibly configured similar to sub-system 250 or sub-system 270 illustrated in FIG. 7B and FIG. 7C, respectively. For example, if column 7a (FIGS. 4, 5 and 7) is a TurboFlow® column as described above and column 7b is an analytical column, then the fluid directed from the loading pump system into valve v1 and column 7a will generally be at a nominal operating pressure of 3-7 MPa and the fluid directed from the eluting pump into valve v2 will generally be at a nominal operating pressure of 30-40 MPa.

In many systems, and as is shown in middle diagram of FIG. 5, the rotary valve v2 of valve system 45 has an internal structure which enables three adjacent ports to be fluidically simultaneously interconnected. This valve structure enables, for instance, separate fluid flows from fluid tubing lines 6n and 6s, respectively from the loading and eluting sub-systems, to be mixed in valve v2 and output, as a mixture, to fluid tubing line 6q. In order to prevent a sudden pressure drop and consequent incorrect flow of fluid when the elution begins, a check valve (not shown) may be provided in the fluidic system between an operative loading pump and the point at which the fluid pathways from the loading pump sub-system and eluting pump sub-system converge. The check valve will not operate so as to permit flow from the loading pump system until the pressure is equalized. Then, with valve v2 configured for elution, the pressure applied by the loading pump is ramped higher as fast as possible until equal pressures exist on both sides of the check valve.

Example 7—Pre-Compression and Pre-Pressurization

Using the LCMS system configurations illustrated in FIGS. 7A-7C, it is occasionally necessary to execute a pre-compression step—prior to directing fluid flow through a chromatographic column—so as to ramp the fluid pressure up to a nominal operating pressure for applications employing the column. In the case of loading analytes onto a TurboFlow® column (described above), the nominal operating pressure and flow rate are generally specified by a user as part of a chromatographic method. However, because of the behavior of the column, some flow-through time is required for the fluid in the column to come up to the correct pressure. As a result of this behavior, the initial flow of sample into the TurboFlow® column may not occur at the user-specified pressure. Accordingly, prior to performing the first step (Step 1) of the user method, the pressure of a pump that is used to load the column may first be directed to a plugged port. With the pump output so configured, the fluid in the pump compressed so as to initially ramp up the pump pressure, prior to directing the sample into the column. Performing this pre-pressurization step allows the entire sample loading step (or other flow-through step, depending on the type of column) to be performed at the correct pressure.

Example 8—Combined Fluid Monitoring and Pump Diagnostics

Figure 17:
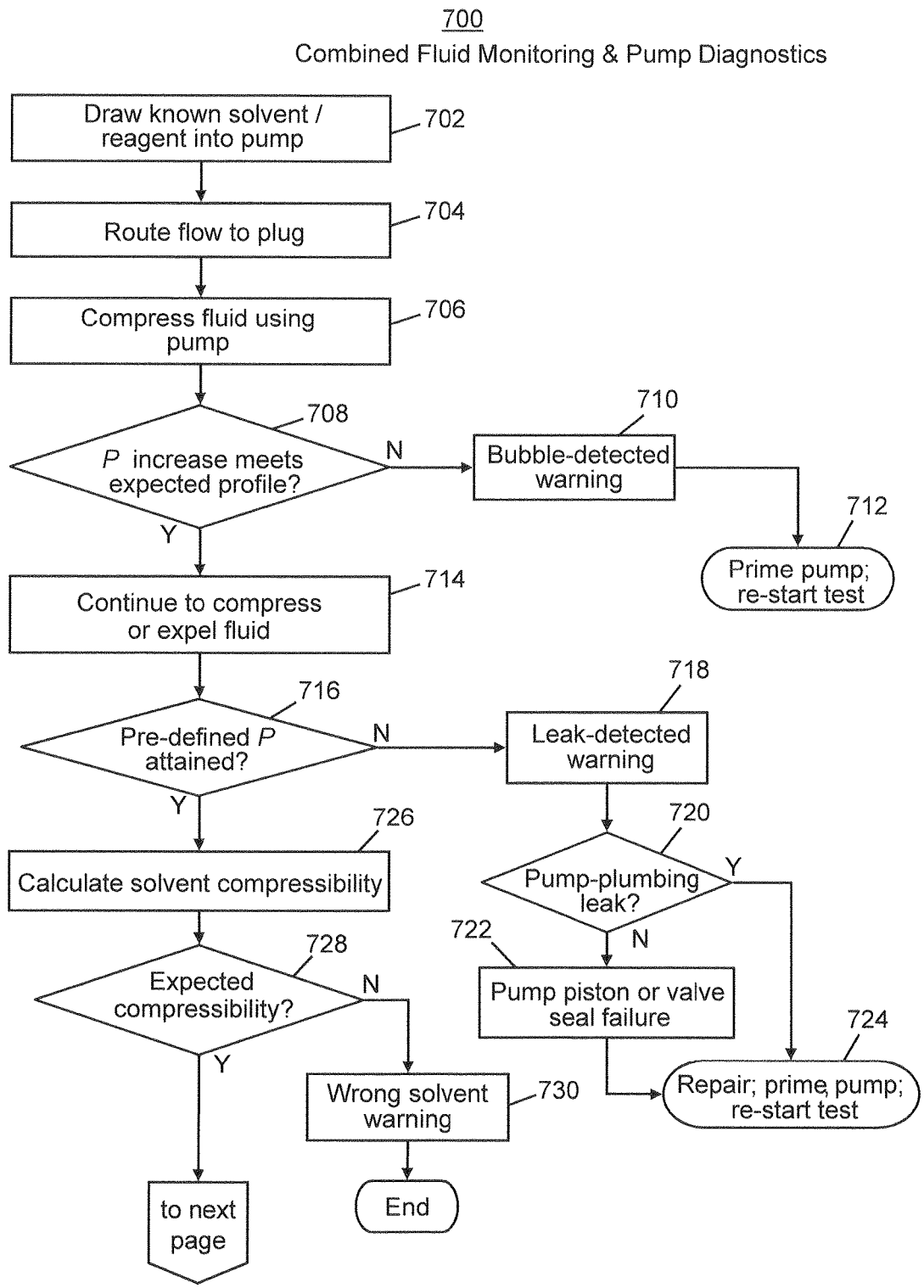
FIG. 17 is a flow diagram of a general method in accordance with the present teachings for performing multiple fluidic identification and pump diagnostic functions.
Figure 17:
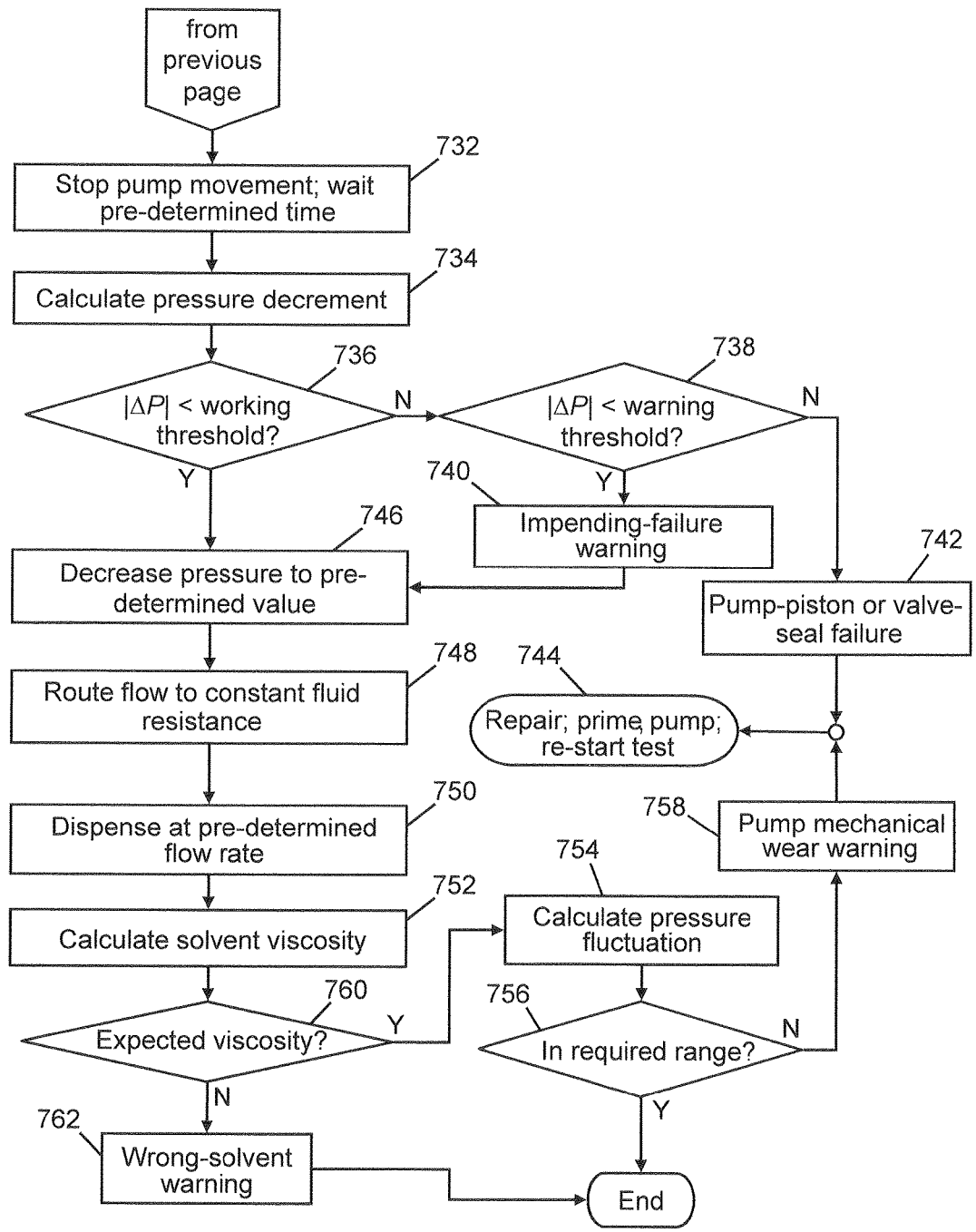

The method 700 illustrated in flowchart form in FIG. 17 combines both fluid monitoring and generation of pump diagnostic information. In the first step, step 702, of the method 700 (FIG. 17), a known solvent or reagent is drawn into a syringe pump. In step 704, the fluid flow is routed to a plugged output port such as, for instance, a port of multiple-port rotary selection valve that is in proximity to the pump. In Step 706, the pump piston is caused to move at a pre-determined rate in a direction which compresses the fluid between the piston and the plug.

In the decision step 708 of the method 700, if the pressure increase meets the expected pressure increase profile—that is, if the pressure increase is not less than that expected from a pre-determined profile, within a tolerance—then pumping continues at Step 714. Otherwise (if the pressure increase is less than that expected), then one or more air or gas bubbles or pockets are interpreted to be present in the fluid pathway and a warning or notification of this condition is provided at Step 710. At this point, the method terminates (Step 712) so that a user or technician may prime the LC system, after which the method may be started again from the beginning.

After a period of continued compression (Step 714), a determination is made (in Step 716) as to whether the pump is capable of achieving some pre-defined pressure. If not, then a leak in either the pump plumbing system or the or the pump (e.g., valve seal or pistion) is interpreted to be present and a warning or notification to this effect is made in Step 718. If the presumed leak is determined not to be in ancillary pump plumbing components (Step 720) than a notification or warning of a pump piston or valve seal failure may be made in Step 722. At this point, the method terminates (Step 724) so that a user or technician may make any necessary repairs and prime the LC system. After making such repairs and priming, the method may be started again from the beginning.

If the pre-defined pressure has been attained, then solvent compressibility is calculated in 726 using the amount of piston movement required to achieve the pre-defined pressure. If the compressibility is not as expected for a presumed solvent or other fluid, then a wrong-solvent warning is provided in step 730 and the method terminates. If, however, the compressibility is determined to be as expected, within a tolerance, then pump movement is stopped (Step 732) and pressure decrease is monitored for a certain pre-determined length of time. The pressure decrement, $|\Delta P|$, is determined in Step 734 and, a subsequent determination is made in Step 736 as to whether this pressure decrement is less than a pre-defined normal working threshold. The normal working threshold is defined such that, if the pressure decrement is less than this threshold, then the pump and any associated components are presumed to be operating normally. If the pressure decrement as calculated in Step 734 is greater than or equal to the working threshold value, then a leak is presumed to be present either in the pump or associated components. If the pressure decrement is further determined, in Step 738, to be greater than or equal to a warning threshold, then a failure has occurred in either the pump or an associated component and a notification to this effect is provided in Step 742. (Note that the warning threshold value is always greater than the normal working threshold value.) After the notification provided in Step 742, the method terminates at Step 744, so that the pump may be repaired or replaced and the system re-primed.

A pressure decrement above the normal working threshold as determined in Step 736 but below the warning threshold as determined in Step 738 is interpreted to mean that a pump component, such as a piston, or a related component, such as a valve seal, while presently still useable, is in danger of failing in the near future. In such a situation, a warning to this effect is provided in Step 740, after which Step 746 is entered.

Step 746 is executed if the pressure decrement is determined to be below the warning threshold. In Step 746, the pressure is decreased to a certain pre-determined value. Then, in Step 748, the flow is routed to a pathway having a constant fluid flow resistance, and caused to flow at a pre-determined flow rate in Step 750 while pressure is monitored. In Step 752, the viscosity of the fluid is calculated using an average monitored pressure. If it is determined (Step 760) that the fluid viscosity is not as expected for a presumed fluid, then a wrong-solvent warning or notification is provided in Step 762 and the method terminated. However, if the calculated viscosity is as expected, within a tolerance, then a pressure fluctuation, versus time or piston movement, is determined (in Step 754) using the pressure variation that was monitored in Step 750. For example, the pressure fluctuation could be similar to the periodic curves 402 and 404 shown in FIG. 10. In this situation, a range of the fluctuation could be determined as the average or possibly maximum peak-to-peak pressure variation or as a standard deviation of the fluctuation or could be determined in some other fashion. Regardless of the method by which the range is characterized, a range greater than a certain pre-determined range threshold, as determined in Step 756, is taken as an indication of excessive mechanical wear in moveable pump parts. Accordingly, a fluctuation range greater than the threshold (Step 756) will cause a mechanical-wear warning or notification to be provided in Step 758, after which the method terminates at Step 744, so that the pump may be repaired or replaced and the system re-primed.

All of the pump-diagnostic methods and system-diagnostic methods described in certain of the examples given above may be performed at certain dedicated system-test times when no chromatographic separations of samples are being run. However, since many liquid chromatography methods necessarily require pre-compression and pressure ramping, the system monitoring can be built in and can occur automatically when running the various user-specified liquid chromatography methods methods.

An improved liquid chromatography system has been disclosed. Advantageously, a system in accordance with the present teachings may be employed in an automated sample preparation and analysis system, such as is disclosed in a co-pending International (PCT) application for patent titled "Automated System for Sample Preparation and Analysis" (Application No. PCT/US11/58452) filed on Oct. 28, 2011 and incorporated herein by reference in its entirety. In various embodiments, the automated sample preparation and analysis system includes a sample preparation system for preparing various samples and a sample analysis system, which may include a liquid chromatography mass spectrometer ("LCMS") for analyzing the prepared samples according to selected analyte assays. The sample preparation system and the sample analysis system are interconnected in an automated manner. The automated sample preparation and analysis system is designed to generally operate with minimal operator intervention or maintenance and includes at least one controller for, inter alia, controlling valve configurations and, optionally, monitoring operational or instrumental conditions. Because of the automated nature of the instrument, it is advantageous for the automated system to be able to monitor its own configuration and operating state and to provide an alert an operator if the system detects any possible problems. A system for liquid chromatography in accordance with the present teachings may assist in these functions.

The discussion included in this application is intended to serve as a basic description. Although the present invention has been described in accordance with the various embodiments shown and described, one of ordinary skill in the art will readily recognize that there could be variations to the embodiments and those variations would be within the spirit and scope of the present invention. The reader should be aware that the specific discussion may not explicitly describe all embodiments possible; many alternatives are implicit. For example, it is easy to envisage that various sub-sets of steps provided in flowcharts herein may be combined with sub-sets of steps from different flowcharts to arrive at augmented or hybridized methods. Accordingly, many modifications may be made by one of ordinary skill in the art without departing from the spirit, scope and essence of the invention. Neither the description nor the terminology is intended to limit the scope of the invention. All patent application disclosures, patent application publications or other publications are hereby explicitly incorporated by reference herein as if fully set forth herein.

What is claimed is:

1. A method of balancing fluid pressure between a first portion and a second portion of a fluidic system of a liquid chromatography system, the first and second fluidic system portions fluidically coupled to first and second inlet ports, respectively, of a first valve that comprises a first configuration by which fluids from both the first and second portions are combined and directed to an outlet line and a second configuration by which only fluid from the second portion is directed to the outlet line, wherein, initially, the first valve is in its second configuration such that only the second portion is initially fluidically coupled to the outlet line at a fluid pressure that is greater than a fluid pressure of the first portion, the method characterized by:

(a) configuring a multiport selection valve of the first portion so as to fluidically couple a syringe pump of the first portion to a port of the multiport selection valve to which is affixed a plug that prevents fluid flow through said port;

(b) compressing a fluid within the syringe pump so that a reading of a first pressure sensor matches a reading of a second pressure sensor, wherein the first and second pressure sensors measure fluid pressure within the first and second portions, respectively;

(c) configuring the multiport selection valve, with the reading of the first pressure sensor matching the reading of the second pressure sensor, so as to fluidically couple the syringe pump to a fluid line of the first portion of the fluidic system and to the first inlet port of the first valve; and (d) placing the first valve in its first configuration such both the first and second portions of the fluidic system are fluidically coupled to the outlet line and to an analytical chromatographic column to which the outlet line is coupled.

2. A method as recited in claim 1, wherein the first portion of the fluidic system includes a second chromatographic column that is fluidically coupled between the multiport selection valve and the first valve.

3. A method as recited in claim 2, wherein the second chromatographic column comprises a cleanup column.

4. A method as recited in claim 1, wherein the initial difference between the fluid pressure of the first portion and the fluid pressure of the second portion is caused by a difference of fluid properties between a fluid within the first portion and a fluid within the second portion.

5. A method as recited in claim 1, wherein the initial difference between the fluid pressure of the first portion and the fluid pressure of the second portion is caused by a difference of flow rates between a fluid within the first portion and a fluid within the second portion.

6. A method of balancing fluid pressure between a first portion and a second portion of a fluidic system of a liquid chromatography system, the first and second fluidic system portions fluidically coupled to first and second inlet ports, respectively, of a first valve that comprises a first configuration by which fluids from both the first and second portions are combined and directed to an outlet line and a second configuration by which only fluid from the second portion is directed to the outlet line, wherein, initially, the first valve is in its second configuration such that only the second portion is initially fluidically coupled to the outlet line at a fluid pressure that is less than a fluid pressure of the first portion, the method characterized by:

(a) configuring a multiport selection valve of the second portion so as to fluidically couple a syringe pump of the second portion to a port of the multiport selection valve to which is affixed a plug that prevents fluid flow through said port;

(b) compressing a fluid within the syringe pump so that a reading of a second pressure sensor matches a reading of a first pressure sensor, wherein the first and second pressure sensors measure fluid pressure within the first and second portions, respectively;

(c) configuring the multiport selection valve, with the reading of the second pressure sensor matching the reading of the first pressure sensor, so as to fluidically couple the syringe pump to a fluid line of the second portion of the fluidic system and to the second inlet port of the first valve; and (d) placing the first valve in its first configuration such both the first and second portions of the fluidic system are fluidically coupled to the outlet line and to an analytical chromatographic column to which the outlet line is coupled.

7. A method as recited in claim 6, wherein the first portion of the fluidic system includes a second chromatographic column that is fluidically coupled between the multiport selection valve and the first valve.

8. A method as recited in claim 7, wherein the second chromatographic column comprises a cleanup column.

9. A method as recited in claim 6, wherein the initial difference between the fluid pressure of the first portion and the fluid pressure of the second portion is caused by a difference of fluid properties between a fluid within the first portion and a fluid within the second portion.

10. A method as recited in claim 6, wherein the initial difference between the fluid pressure of the first portion and the fluid pressure of the second portion is caused by a difference of flow rates between a fluid within the first portion and a fluid within the second portion.

* * * * *